(12) United States Patent
Zhang

(10) Patent No.: US 10,513,488 B2
(45) Date of Patent: Dec. 24, 2019

(54) METHODS OF MANUFACTURING BENZOQUINOLINE COMPOUNDS

(71) Applicant: Auspex Pharmaceuticals, Inc., La Jolla, CA (US)

(72) Inventor: Chengzhi Zhang, San Diego, CA (US)

(73) Assignee: AUSPEX PHARMACEUTICALS, INC., North Wales, PA (US)

( * ) Notice: Subject to any disclaimer, the term of this patent is extended or adjusted under 35 U.S.C. 154(b) by 0 days.

(21) Appl. No.: 15/472,779

(22) Filed: Mar. 29, 2017

(65) Prior Publication Data

US 2017/0197957 A1  Jul. 13, 2017

Related U.S. Application Data

(63) Continuation of application No. 14/551,909, filed on Nov. 24, 2014, now abandoned.

(60) Provisional application No. 61/911,214, filed on Dec. 3, 2013.

(51) Int. Cl.

| C07D 217/04 | (2006.01) |
| C07D 455/06 | (2006.01) |
| C07C 231/12 | (2006.01) |
| C07C 231/02 | (2006.01) |
| C07C 221/00 | (2006.01) |
| C07B 59/00 | (2006.01) |

(52) U.S. Cl.
CPC .......... *C07C 231/12* (2013.01); *C07B 59/001* (2013.01); *C07B 59/002* (2013.01); *C07C 221/00* (2013.01); *C07C 231/02* (2013.01); *C07D 217/04* (2013.01); *C07D 455/06* (2013.01); *C07B 2200/05* (2013.01)

(58) Field of Classification Search
CPC .. C07D 455/06; C07B 59/002; C07B 2200/05
USPC .......................................................... 546/95
See application file for complete search history.

(56) References Cited

U.S. PATENT DOCUMENTS

| 2,830,993 | A | 4/1958 | Brossi et al. |
| 2,843,591 | A | 7/1958 | Brossi et al. |
| 3,045,021 | A | 7/1962 | Brossi |
| 4,193,998 | A | 3/1980 | Szantay et al. |
| 4,316,897 | A | 2/1982 | Lotz |
| 4,678,792 | A | 7/1987 | Nickl et al. |
| 5,451,409 | A | 9/1995 | Rencher et al. |
| 6,221,335 | B1 | 4/2001 | Foster |
| 6,287,599 | B1 | 9/2001 | Burnside et al. |
| 6,440,710 | B1 | 8/2002 | Keinan et al. |
| 6,488,962 | B1 | 12/2002 | Berner et al. |
| 6,603,008 | B1 | 8/2003 | Ando et al. |
| 7,517,990 | B2 | 4/2009 | Ito et al. |
| 7,897,768 | B2 | 3/2011 | Rishel et al. |
| 7,976,870 | B2 | 7/2011 | Berner et al. |
| 8,008,500 | B2 | 8/2011 | Rishel et al. |
| 8,053,578 | B2 | 11/2011 | Rishel et al. |
| 8,524,733 | B2 | 9/2013 | Gant et al. |
| 9,233,959 | B2 * | 1/2016 | Sommer .............. A61K 9/0065 |
| 2002/0013372 | A1 | 1/2002 | Ekins |
| 2005/0064034 | A1 | 3/2005 | Li et al. |
| 2007/0197695 | A1 | 8/2007 | Potyen et al. |
| 2008/0033011 | A1 | 2/2008 | Tung |
| 2008/0050312 | A1 | 2/2008 | Kung et al. |
| 2008/0167337 | A1 | 7/2008 | Gano |
| 2008/0212839 | A1 | 9/2008 | Salla et al. |
| 2008/0299204 | A1 | 12/2008 | Nangia et al. |
| 2009/0018191 | A1 | 1/2009 | Alken et al. |
| 2009/0142265 | A1 | 6/2009 | Rishel et al. |
| 2009/0297599 | A1 | 12/2009 | Viragh et al. |
| 2010/0055133 | A1 | 3/2010 | Duffield et al. |
| 2010/0113496 | A1 | 5/2010 | Gant |
| 2010/0130408 | A1 | 5/2010 | Kohjima et al. |
| 2010/0130480 | A1 | 5/2010 | Gant |
| 2010/0189698 | A1 | 7/2010 | Willis |

(Continued)

FOREIGN PATENT DOCUMENTS

| CN | 102120742 A | 7/2011 |
| CN | 102260255 A | 11/2011 |

(Continued)

OTHER PUBLICATIONS

Zheng, G et al., Vesicular Monoamine Transporter 2: Role as a Novel Target for Drug Development, The AAPS Journal 2006; 8 (4) Article 78.

(Continued)

*Primary Examiner* — Rita J Desai

(74) *Attorney, Agent, or Firm* — BakerHostetler

(57) ABSTRACT

The present invention relates to new methods of manufacturing benzoquinoline inhibitors of vesicular monoamine transporter 2 (VMAT2), and intermediates thereof.

Formula I

37 Claims, No Drawings

(56) References Cited

U.S. PATENT DOCUMENTS

| | | |
|---|---|---|
| 2010/0204258 A1 | 8/2010 | Harris et al. |
| 2011/0053866 A1 | 3/2011 | Duffield et al. |
| 2011/0118300 A1 | 5/2011 | Harris et al. |
| 2011/0182818 A1 | 7/2011 | Fallon |
| 2011/0206782 A1 | 8/2011 | Zhang |
| 2012/0003330 A1 | 1/2012 | Gant et al. |
| 2012/0053159 A1 | 3/2012 | Muller et al. |
| 2012/0077839 A1 | 3/2012 | Gano |
| 2012/0081031 A1 | 4/2012 | Kameyama et al. |
| 2013/0116215 A1 | 5/2013 | Coma et al. |
| 2013/0197067 A1 | 8/2013 | Anderson et al. |
| 2013/0197227 A1 | 8/2013 | Min et al. |
| 2013/0296360 A1 | 11/2013 | Gant et al. |
| 2014/0206712 A1 | 7/2014 | Gant et al. |
| 2014/0206713 A1 | 7/2014 | Gant et al. |
| 2014/0336386 A1 | 11/2014 | Sommer et al. |
| 2014/0341994 A1 | 11/2014 | Sommer et al. |
| 2014/0350044 A1 | 11/2014 | Gant et al. |
| 2015/0004231 A1 | 1/2015 | Sommer et al. |
| 2015/0080426 A1 | 3/2015 | Gant et al. |
| 2015/0080427 A1 | 3/2015 | Gant et al. |

FOREIGN PATENT DOCUMENTS

| | | | |
|---|---|---|---|
| CN | 102936246 A | | 2/2013 |
| EP | 1716145 B1 | | 8/2008 |
| EP | 2326643 B1 | | 5/2013 |
| GB | 999095 | * | 7/1965 |
| IN | 201204923 | | 11/2012 |
| JP | 2012-503010 A | | 2/2012 |
| JP | 2013-527237 | | 6/2013 |
| WO | 95/26325 A2 | | 10/1995 |
| WO | 00/08020 A2 | | 2/2000 |
| WO | 2005/051389 A1 | | 6/2005 |
| WO | 2005/077946 A1 | | 8/2005 |
| WO | 2006/053067 A2 | | 5/2006 |
| WO | 2006/078846 A1 | | 7/2006 |
| WO | 2007/130365 A2 | | 11/2007 |
| WO | 2008/058261 A1 | | 5/2008 |
| WO | 2008/064274 A1 | | 5/2008 |
| WO | 2008/112278 A2 | | 9/2008 |
| WO | 2008/154243 A1 | | 12/2008 |
| WO | 2009/003226 A1 | | 1/2009 |
| WO | 2009/070552 A1 | | 6/2009 |
| WO | 2009/124357 A1 | | 10/2009 |
| WO | 2010/018408 A2 | | 2/2010 |
| WO | 2010/044981 A2 | | 4/2010 |
| WO | 2011/019956 A2 | | 2/2011 |
| WO | 2011/106248 A2 | | 9/2011 |
| WO | 2011/153157 A2 | | 12/2011 |
| WO | 2012/079022 A1 | | 6/2012 |
| WO | 2012/081031 A1 | | 6/2012 |
| WO | 2013/142816 A1 | | 9/2013 |
| WO | 2014/047167 A1 | | 3/2014 |
| WO | 2014/120654 A1 | | 8/2014 |
| WO | 2015/048370 A1 | | 4/2015 |
| WO | 2015/077520 A1 | | 5/2015 |
| WO | 2015/077521 A1 | | 5/2015 |
| WO | 2015/084622 A1 | | 6/2015 |
| WO | 2015/112707 A1 | | 7/2015 |

OTHER PUBLICATIONS

Yao et al., Preparation and evaluation of tetrabenazine enantiomers and all eight stereoisomers of dihydrotetrabenazine as VMAT2 inhibitors, Eur. J. Med. Chem, 2011, 46, 1841-1848.

Wolen et al.; The Application of Stable Isotopes to Studies of Drug Bioavailibility and Bioequivalence, J. Clin. Pharmacol., 1986, 26, 419-424.

Wingstrand et al., Bioavailability from felodipine extended-release tablets with different dissolution properties, Int. J. Pharmaceutics, 1990, 60, 151-156.

Toronto Research Chemicals, Inc., Tetrabenazine-d7, http://www.trc-canada.com/details.php?CatNumber=T284002. Downloaded 2009.

Tonn et al.; Simultaneous Analysis of Diphenylhydramine and a Stable Isotope Analog (2H10) Diphenylhydramine Using Capillary Gas Chromatography With Mass Selective Detection in Biological Fluids From Chronically Instrumented Pregnant Ewes, Biomedical Mass Spectrometry, 1993, 22, 633-642.

Synthesis of Emetine and Related compounds, Openshaw and Whittaker. 1963.

Sommer et al., Benzoquinolone Inhibitors of VMAT2, Auspex Pharmaceuticals, Inc., WO2014120654A 1, International Preliminary Report on Patentability, publication date Aug. 4, 2015.

Scifinder Database Search, Dihydrotetrabenazine Scifinder Structure Search, Search Performed on May 22, 2010.

Schwartz, DE et al., Metabolic studies of tetrabenazine, a psychotropic drug in animals and man, Biochemical Pharmacology, 1966, 15, 645-655.

Roberts, MS et al., the Pharmacokinetics of Tetrabenazine and its Hydroxy Metabolite in Patients Treated for Involuntary Movement Disorders, Eur J Clin Pharmacol (1986) 29: 703-708.

Rishel et al., Asymmetric synthesis of Tetrabenazine and Dihydrotetrabenazine, J. Org. Chem., 2009, 74, 4001-04.

Rampe, D et al.; Deuterated Analogs of verapamil and nifedipine. Synthesis and biological activity, Eur J Med Chem (1993) 28, 259-263.

Pubchem, Compound Summary for AGN-PC-01VNZU, https://pubchem.ncbi.nlm.nfttgov/compoundll84l2o75> entire document, created Jan. 16, 2012.

Pubchem, Compound Summary for 54765059, https-J/pubchem.ncbi.nlm.nih.gov/compound/54765059>. entire locument, created Jan. 16, 2012.

Popp, FD et al., Synthesis of potential antineoplastic agents XXVI: 1,3,4,6,7,11b-hexahydro-9,10- dimethoxy-2H-benzo[a]2-quinolizinone derivatives, Journal of Pharmaceutical Sciences, 1978, 67(6), 871-873.

Pohl, LR et al.; Determination of toxic Pathways of Metabolism by Deuterium Substitution, Drug Metabolism Rev 1985, 1335.

Pieiaszek et al.; Moricizine Bioavailability via Simultaneous, Dual, Stable Isotope Administration: Bioequivalence Implications, J. Clin. Pharmacol., 1999, 39, 817-825.

Paleacu et al., Tetrabenazine Treatment in Movement Disorders, Clin. Neuropharmacol., 2004, 27(5), 230-233.

Nutt et all., Evidence-based guidelines for management of attention-deficit/hyperactivity disorder in adolescents in transition to adult services and in adults: recommendations from the British Association for Psvchopharmacoloav, J Psvchopharmacol. Jan. 2007;21(1):10-41. Epub Nov. 8, 2006.

Nelson, SD et al.; The Use of Deuterium Isotope Effect to Probe the Active Site Properties, Mechanism of Cytochrome P450-catalyzed Reactions, and Mechanisms of Metabolically Dependent Toxicity, Drug Metabolism and Disposition 31:1481-1498, 2003.

Nelson, SD et al.; Primary and B-Secondary Deuterium Isotope Effects in N-Deethylation Reactions, Journal of Medicinal Chemistry, 1975, vol. 18, No. 11.

Mehvar, R et al., Pharmacokinetics of Tetrabenazine and Its Major Metabolite in Man and Rat Bioavailability and Dose Dependency Studies, Drug Met Disp. 1987, 15(2), 250-255.

Mamada, Ket al.; Pharmacokinetic Equivalence of Deuterium-Labeled and Unlabeled Phenytoin, Drug Metabolism and Disposition, 1986, 14(4), 509-11.

Lundbeck, Inc., Xenazine Prescibing Information, 2008.

Lee, H et al.; Deuterium Magic Angle Spinning Studies of Substrates Bound to Cytochrome P450, Biochemistry 1999, 38, 10808-10813.

Lee et al., In Vitro and in Vivo Studies of Benzisoquinoline Ligands for the Brain Synaptic Vesicle Monoamine Transporter, Journal Med. Chem. ,1996, 39, 191-96.

Kushner, DJ et al.; Pharmacological uses and perspectives of heavy water and deuterated compounds, Can J Phys Pharm 1999, 77, 79-88.

Kilbourn, MR et al., Absolute Configuration of (+)-a-Dihydrotetrabenazine, an Active Metabolite of Tetrabenazine, Chirality 9:59-62 1997.

(56) References Cited

OTHER PUBLICATIONS

Kilbourn et al., Binding of alpha-Dihydrotetrabenazine to the Vesicular Monoamine Transporter is Stereospecific, Eur. J. Pharmacol., 1995, 278, 249-52.
Kenny C et al., Tetrabenazine in the treatment of hyperkinetic movement disorders, Informa Healthcare, 2006, vol. 6, No. 1 ,pp. 7-17.
Jindal et al., Mass Spectrometric Determination of Tetrabenazine Using a Stable Isotope-labeled Analogue as an Internal Standard, Jindal et al., J. Chromatography, 1989, 493, 392-97.
Honma et al.; The Metabolism of Roxatidine Acetate Hydrochloride, Drug Metabolism and Disposition, 1987, 15(4), 551-559.
Helfenbein, J et al.; Isotopic Effect Study of Propofol Deuteration on the Metabolism, Activity, and Toxicity of the Anesthetic, J. Med. Chem. 2002, 45, 5806-5808.
Haskins, N.J.; The Application of Stable Isotopes in Biomedical Research, Biomedical Mass Spectrometry, 1982, 9(7), 269-277.
Gouyette, Alain; Use of Deuterium-Labelled Elliptinium and Its Use in Metabolic Studies, Biomedical and Environmental Mass Spectrometry, 1988, 15, 243-247.
Goswami et al., Fluoroalkyl derivatives of dihydrotetrabenazine as positron emission tomography imaging agents targeting vesicular monoamine transporters, Nucl. Met Biol., 2006, 33, 685-694.
Gant et al., Formulations Pharmacokinetics of Deuterated Benzoquinoline Inhibitors of Vesicular Monoamine Transporter 2, Auspex Pharmaceuticals, Inc., WO2014047167 A1, International Preliminary Report on Patentability, dated Mar. 27, 2014.
Gant et al., Formulations Pharmacokinetics of Deuterated Benzoquinoline Inhibitors of Vesicular Monoamine Transporter 2, Auspex Pharmaceuticals, Inc., US20140341994A1, Non-Final Rejection, dated Nov. 28, 2014.
Gant et al., Formulations Pharmacokinetics of Deuterated Benzoquinoline Inhibitors of Vesicular Monoamine Transporter 2, Auspex Pharmaceuticals, Inc., US20140341994A1, Non-Final Rejection, dated Oct. 29, 2014.
Gant et al., Formulations Pharmacokinetics of Deuterated Benzoquinoline Inhibitors of Vesicular Monoamine Transporter 2, Auspex Pharmaceuticals, Inc., US20140336386A1, Non-Final Rejection, dated Nov. 28, 2014.
Gant et al., Formulations Pharmacokinetics of Deuterated Benzoquinoline Inhibitors of Vesicular Monoamine Transporter 2, Auspex Pharmaceuticals, Inc., US 20150004231 A1, Notice of Allowance and Fees Due, dated Apr. 15, 2015.
Gant et al., Formulations Pharmacokinetics of Deuterated Benzoquinoline Inhibitors of Vesicular Monoamine Transporter 2, Auspex Pharmaceuticals, Inc., US 20150004231 A1, Non-Final Rejection, dated Oct. 29, 2014.
Gant et al., Benzoquinoline Inhibitors of VMAT2, WO 2011106248 International Preliminary Report on Patentability, Auspex Pharmaceuticals, Inc., dated Sep. 1, 2011.
Gant et al., Benzoquinoline Inhibitors of VMAT2, Auspex Pharmaceuticals, Inc., WO2011153157A2, International Preliminary Report on Patentability, publication date Dec. 4, 2012.
Gant et al., Benzoquinoline Inhibitors of VMAT2, Auspex Pharmaceuticals, Inc., US 20150080426 A1, Non-Final Rejection, dated Feb. 6, 2015.
Gant et al., Benzoquinoline Inhibitors of VMAT2, Auspex Pharmaceuticals, Inc., US 20150080426 A1, Examiner initiated interview summary, dated Feb. 6, 2015.
Gant et al., Benzoquinoline Inhibitors of VMAT2, Auspex Pharmaceuticals, Inc., US 20120003330 A1, Non-Final Rejection, dated Jan. 16, 2014.
Gant et al., Benzoquinoline Inhibitors of Vesicular Monoamine Transporter 2, WO 2010044981 International Preliminary Report on Patentability, Auspex Pharmaceuticals, Inc. dated Apr. 22, 2010.
Gant et al., Benzoquinoline Inhibitors of Vesicular Monoamine Transporter 2, US20150080427 A1, Non-Final Rejection, dated Dec. 29, 2014.
Gant et al., Benzoquinoline Inhibitors of Vesicular Monoamine Transporter 2, US20150080427 A1, Final Rejection, dated Aug. 11, 2015.
Gant et al., Benzoquinoline Inhibitors of Vesicular Monoamine Transporter 2, U.S. Appl. No. 14/454,911, Affidavit-traversing rejections or objections rule 132, dated Dec. 15, 2014.
Gant et al., Benzoquinoline Inhibitors of Vesicular Monoamine Transporter 2, U.S. Appl. No. 14/225,010, Affidavit-traversing rejections or objections rule 132, dated Jul. 30, 2014.
Gant et al., Benzoquinoline Inhibitors of Vesicular Monoamine Transporter 2, US12562621, Affidavit-traversing rejections or objections rule 132, Jun. 19, 2013; also submitted in Gant et al., Benzoquinoline Inhibitors of Vesicular Monoamine Transporter 2 , U.S. Appl. No. 13/934,960, Affidavit-traversinq rejections or objections rule 132, Mar. 17, 2014.
Gant et al., Benzoquinoline Inhibitors of Vesicular Monoamine Transporter 2, Auspex Pharmaceuticals, Inc., U.S. Pat. No. 8,524,733B2, Notice of Allowance and Fees Due, dated Jun. 28, 2013.
Gant et al., Benzoquinoline Inhibitors of Vesicular Monoamine Transporter 2, Auspex Pharmaceuticals, Inc., U.S. Pat. No. 8,524,733B2, Non Final Rejection, dated Apr. 10, 2012.
Gant et al., Benzoquinoline Inhibitors of Vesicular Monoamine Transporter 2, Auspex Pharmaceuticals, Inc., U.S. Pat. No. 8,524,733B2, Final Rejection, dated Nov. 5, 2012.
Gant et al., Benzoquinoline Inhibitors of Vesicular Monoamine Transporter 2, Auspex Pharmaceuticals, Inc., U.S. Pat. No. 8,524,733B2, Examiner initiated interview summary, dated Jun. 28, 2013.
Gant et al., Benzoquinoline Inhibitors of Vesicular Monoamine Transporter 2, Auspex Pharmaceuticals, Inc., U.S. Pat. No. 8,524,733B2, Applicant Initiated Interview Summary, dated Apr. 24, 2013.
Gant et al., Benzoquinoline Inhibitors of Vesicular Monoamine Transporter 2, Auspex Pharmaceuticals, Inc., US 20140350044 A1, Notice of Allowance, dated Jan. 13, 2015.
Gant et al., Benzoquinoline Inhibitors of Vesicular Monoamine Transporter 2, Auspex Pharmaceuticals, Inc., US 20140350044 A1, Non-Final Rejection, dated Sep. 15, 2014.
Gant et al., Benzoquinoline Inhibitors of Vesicular Monoamine Transporter 2, Auspex Pharmaceuticals, Inc., US 20140350044 A1, Examiner initiated interview summary, dated Jan. 13, 2015.
Gant et al., Benzoquinoline Inhibitors of Vesicular Monoamine Transporter 2, Auspex Pharmaceuticals, Inc., US 20140206713 A1, Notice of Allowance, dated Dec. 16, 2014.
Gant et al., Benzoquinoline Inhibitors of Vesicular Monoamine Transporter 2, Auspex Pharmaceuticals, Inc., US 20140206713 A1, Non-Final Rejection, dated Apr. 30, 2014.
Gant et al., Benzoquinoline Inhibitors of Vesicular Monoamine Transporter 2, Auspex Pharmaceuticals, Inc., US 20140206713 A1, Final Rejection, dated Sep. 8, 2014.
Gant et al., Benzoquinoline Inhibitors of Vesicular Monoamine Transporter 2, Auspex Pharmaceuticals, Inc., US 20140206712 A1, Non-Final Rejection, dated Dec. 3, 2014.
Gant et al., Benzoquinoline Inhibitors of Vesicular Monoamine Transporter 2, Auspex Pharmaceuticals, Inc., US 20140206712 A1, Final Rejection, dated Jan. 23, 2015.
Gant et al., Benzoquinoline Inhibitors of Vesicular Monoamine Transporter 2, Auspex Pharmaceuticals, Inc., US 20140206712 A1, Examiner initiated interview summary, dated Jan. 23, 2015.
Gant et al., Benzoquinoline Inhibitors of Vesicular Monoamine Transporter 2, Auspex Pharmaceuticals, Inc., US 20130296360 A1, Non-Final Rejection, dated Sep. 18, 2013.
Gant et al., Benzoquinoline Inhibitors of Vesicular Monoamine Transporter 2, Auspex Pharmaceuticals, Inc., US 20130296360 A1, Final Rejection, dated Apr. 16, 2014.
Gant et al., Benzoquinoline Inhibitors of Vesicular Monoamine Transporter 2, Auspex Pharmaceuticals, Inc., US 20130296360 A1, Examiner initiated interview summary, dated Apr. 16, 2014.
Foster, AB; Deuterium Isotope Effects in Studies of Drug Metabolism, Trends in Pharmacological Sciences, Dec. 1984, 524-7.
Foster, A.B., Deuterium Isotope Effects in the Metabolism of Drugs and Xenobiotics: Implications for Drug Design, Adv. Drug Res., Academic Press, London, GB, vol. 14, Jan. 1, 1985, pp. 1-40.

(56) References Cited

OTHER PUBLICATIONS

Fisher, MB, et al.;The complexities inherent in attempts to decrease drug clearance by blocking sites of GYP-mediated metabolism, Curr Opin Drug Discov Develop; 2006, 9(1), 101-9.

Farmer, PB, et al.;Synthesis, Metabolism, and Antitumor Activity of Deuterated Analogues of 1-(2-Choloroethyl)-3-cyclohexyl-1-nitrosourea, Journal of Medicinal Chemistry, 1978, vol. 21, No. 6, 514-20.

Elison, C et al.;Effect of Deuteration of N-CH$_{3}$ Group on Potency and Enzymatic N-Demethylation of Morphine, Science, 1961, 134(3485), 1078-9.

Dyck et al.; Effects of Deuterium Substitution on the Catabolism of Beta-Phenethylamine: An In Vivo Study, J. Neurochem., 1986, 46(2), 399-404.

Duffield et al., Pharmaceutical Compositions, WO 2010/018408- International Preliminary Report on Patentability, Biovail Laboratories International, Feb. 18, 2010.

DaSilva, JN et al., Synthesis of [11C]Tetrabenazine, a Vesicular Monoamine Uptake Inhibitor, for PET Imaging Studies, Appl. Radiat. Isot. vol. 44, No. 4, pp. 673-676, 1993.

Cis (2,3)-Dihydro Tetrabenazine-d6, Chemical Book, Jan. 1, 2009 (Jan. 1, 2009).

Cherrah et al.; Study of Deuterium Isotope Effects on Protein Binding by Gas Chromatography/Mass Spectrometry. Caffeine and Deuterated Isomers, Biomedical and Environmental Mass Spectrometry, 1987, 14, 653-657.

Cheng Wu et al , Synthesis of 6-Nitro-L-DOPA, Chinese Journal of Synthetic Chemistry, vol. 19, No. 3, pp. 418-420, 2011.

Buteau K C., Deuterated Drugs: Unexpectedly Nonobvious, Buteau K. C.,J. High Tech. L, 2009, pp. 22-74.

Burm, AGL et al.; Pharmacokinetics of Lidocaine and bupivacaine and stable isotope-labeled analogs: a study in healthy volunteers, Biopharmaceutics and Drug Disposition, 1988, 9, 85-95.

Browne, Thomas; Stable Isotope Techniques in Early Drug Development: An Economic Evaluation, J. Clin. Pharmacol., 1998, 38, 213-220.

Browne, T.R.; Chapter 2. Isotope Effect: Implications for Pharmaceutical Investigations, Pharm Lib 13, 1997.

Browne, T.R. et al.; Pharmacokinetic Equivalence of Stable-Isotope-Labeled and Unlabeled Drugs. Phenobarbital in Man, J Clin Pharmacol, 1982, 22, 309-315.

Borgstrom, L et al.; Comparative Pharmacokinetics of Unlabeled and Deuterium-Labeled Terbutaline: Demonstration of a Small Isotope Effect, J Pharm Sci, 1988, 77(11), 952-4.

Bauer, LA et. al.; Olnfluence of long-term infusions on lidocaine kinetics, Clin. Pharmacol. Ther. 1982, 433-7.

Baillie, Thomas, The Use of Stable Isotopes in Pharmaceutical Research, Pharmacological Reviews, 1981, 33(2), 81-132.

Abrahamsson et al., Absorption, Gastrointestinal Transit, and Tablet Erosion of Felodipine Extended-Release (ER) Tablets, Pharmaceutical Rsearch, 1993, 10(5) 709-714.

A Study of the Effectiveness and safety of Tetrabenazine MR in Pediatric Subjects With Tourette's Syndrome (TBZ-MR), https://clinicaltrials.gov/ct2/show/NCT01133353?term=tetrabenazine&rank=3, Downloaded Feb. 16, 2015.

Wu Cheng et al Synthesis of 6-Nitro-L-DOPA (Year: 2010).

Savani et al., Neurology 2007, 68(10), 797.

Kilbourn et al., Chirality, 1997, (9), 59-62.

Kenney et al., Expert Review of Neurotherapeutics 2006, 6(1), 7-17.

Ivanov et al., Heterocycles 2001, 55(8), 1569-1572.

Boldt et al., Synth. Commun., 2009, (39), 3574-3585.

Berge et al.,/. Pharm. Sci. 1977, 66, 1-19.

Zhao Bao-Xiang et al: Synthesis of nitrones from 3,4-dihydroisoquinoline derivatives by oxidation with m-chloroperoxybenzoic acid. Organic Preparations and Procedures International: The New Journal for Organic Synthesis, 1997, vol. 29(2), pp. 185-194.

SCHEMBL6815570, Pubchem, Database accession No. GN-PC-01VNZU, URL: NCBI; PubChem CID: 18412075; 14 pages.

* cited by examiner

METHODS OF MANUFACTURING BENZOQUINOLINE COMPOUNDS

This application is a continuation of U.S. Ser. No. 14/551,909, filed Nov. 24, 2014, which claims the benefit of priority of U.S. Provisional Application No. 61/911,214, filed Dec. 3, 2013, the disclosures of which are hereby incorporated by reference as if written herein in their entireties.

Disclosed herein are methods of manufacturing benzoquinoline compounds, and intermediates thereof.

Tetrabenazine (Nitoman, Xenazine, Ro 1-9569), 1,3,4,6,7,11b-Hexahydro-9,10-dimethoxy-3-(2-methylpropyl)-2H-benzo[a]quinoline, is a vesicular monoamine transporter 2 (VMAT2) inhibitor. Tetrabenazine is commonly prescribed for the treatment of Huntington's disease (Savani et al., *Neurology* 2007, 68(10), 797; and Kenney et al., *Expert Review of Neurotherapeutics* 2006, 6(1), 7-17).

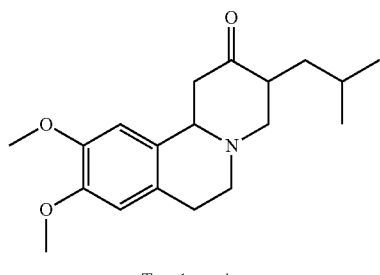

Tetrabenazine $d_6$-Tetrabenazine is a deuterated analog of tetrabenazine which has improved pharmacokinetic properties when compared to the non-deuterated drug and is currently under clinical development. U.S. Pat. No. 8,524,733.

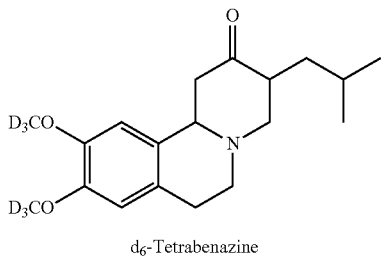

$d_6$-Tetrabenazine

Deuterium Kinetic Isotope Effect

Tetrabenazine is a VMAT2 inhibitor. The carbon-hydrogen bonds of tetrabenazine contain a naturally occurring distribution of hydrogen isotopes, namely $^1H$ or protium (about 99.9844%), $^2H$ or deuterium (about 0.0156%), and $^3H$ or tritium (in the range between about 0.5 and 67 tritium atoms per $10^{18}$ protium atoms). Increased levels of deuterium incorporation may produce a detectable Deuterium Kinetic Isotope Effect (DKIE) that could affect the pharmacokinetic, pharmacologic and/or toxicologic profiles of tetrabenazine in comparison with tetrabenazine having naturally occurring levels of deuterium.

Based on discoveries made in our laboratory, as well as considering the literature, tetrabenazine is metabolized in humans at the isobutyl and methoxy groups. The current approach reduces metabolism at some or all of these sites. Limiting the production of these metabolites has the potential to decrease the danger of the administration of such drugs and may even allow increased dosage and/or increased efficacy. All of these transformations can occur through polymorphically-expressed enzymes, exacerbating interpatient variability. Further, some disorders are best treated when the subject is medicated around the clock or for an extended period of time. For all of the foregoing reasons, a medicine with a longer half-life may result in greater efficacy and cost savings. Various deuteration patterns can be used to (a) reduce or eliminate unwanted metabolites, (b) increase the half-life of the parent drug, (c) decrease the number of doses needed to achieve a desired effect, (d) decrease the amount of a dose needed to achieve a desired effect, (e) increase the formation of active metabolites, if any are formed, (f) decrease the production of deleterious metabolites in specific tissues, and/or (g) create a more effective drug and/or a safer drug for polypharmacy, whether the polypharmacy be intentional or not. The deuteration approach has demonstrated the ability to slow the metabolism of tetrabenazine and attenuate interpatient variability.

Novel methods of manufacturing benzoquinoline compounds, including tetrabenazine and deuterated tetrabenazine analogs such as $d_6$-tetrabenazine are disclosed herein.

In certain embodiments of the present invention, disclosed herein is a process of preparing a compound of Formula IV:

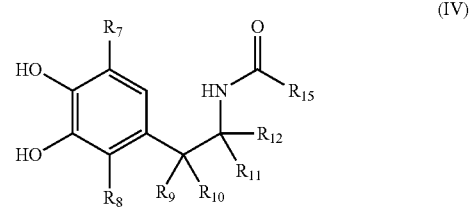

(IV)

or a salt thereof, comprising:
a step of reacting a compound of Formula II or a salt thereof with a compound of Formula III:

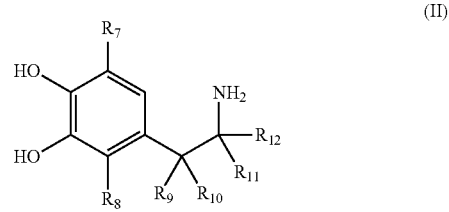

(II)

(III)

in the presence of a base;
wherein:
$R_7$-$R_{12}$ and $R_{15}$ are independently selected from the group consisting of hydrogen and deuterium; and
$Y_1$ is selected from the group consisting of acetoxy, alkoxy, halogen, haloalkoxy, perhaloalkoxy, heteroalkoxy, and aryloxy, any of which may be optionally substituted.

In certain embodiments, $Y_1$ is acetoxy.
In certain embodiments, $Y_1$ is $C_1$-$C_4$ alkoxy.

In certain embodiments, $Y_1$ is ethoxy.

In certain embodiments, $Y_1$ is selected from the group consisting of fluorine, chlorine, and bromine.

In certain embodiments, said base is selected from the group consisting of alkali metal alkoxides, alkali metal hydroxides, alkali metal hydrides, alkali metal carbonates, and trialkylamines.

In certain embodiments, said base is an alkali metal alkoxide.

In certain embodiments, said base is sodium tert-butoxide.

In certain embodiments, $Y_1$ is ethoxy.

In certain embodiments, disclosed herein is a process of preparing a compound of Formula VI:

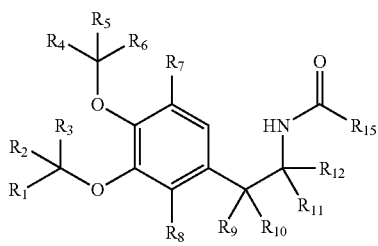

(VI)

comprising:
a step of reacting a compound of Formula IV or a salt thereof with a compound of Formula V:

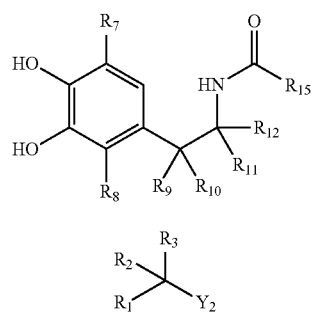

(IV)

(V)

in a solvent and in the presence of a base;
wherein:
$R_1$-$R_{12}$ and $R_{15}$ are independently selected from the group consisting of hydrogen and deuterium; and
$Y_2$ is selected from the group consisting of halogen, alkyl sulfate, alkyl sulfonate, halosulfonate, perhaloalkyl sulfonate, aryl sulfonate, alkylaryl sulfonate, dialkyloxonium, alkylphosphate, and alkylcarbonate, any of which may be optionally substituted.

In certain embodiments, $Y_2$ is iodide or methylsulfate.

In certain embodiments, $Y_2$ is iodide.

In certain embodiments, said base is selected from the group consisting of alkali metal carbonates, alkali metal bicarbonates, alkali metal alkoxides, alkali metal hydroxides, alkali metal hydrides, and trialkylamines.

In certain embodiments, said base is an alkali metal carbonate.

In certain embodiments, said base is potassium carbonate.

In certain embodiments, said solvent is selected from the group consisting of acetone, acetonitrile, dimethyl formamide, 2-methyltetrahydrofuran, and tetrahydrofuran.

In certain embodiments, said solvent is acetone.

In certain embodiments, the volume of said solvent is between about 5 to about 15 times the mass of the compound of Formula IV.

In certain embodiments, the volume of said solvent is between about 6 to about 10 times the mass of the compound of Formula IV.

In certain embodiments, the volume of said solvent is about 8 times the mass of the compound of Formula IV.

In certain embodiments, said reaction step is carried out in the presence of a phase transfer catalyst.

In certain embodiments, said phase transfer catalyst is selected from the group consisting of tetrabutylammonium bromide, tetrabutylammonium iodide, and 18-crown-6.

In certain embodiments, said phase transfer catalyst is tetrabutylammonium bromide.

In certain embodiments, disclosed herein is a process of preparing a solid salt of a compound of Formula VII:

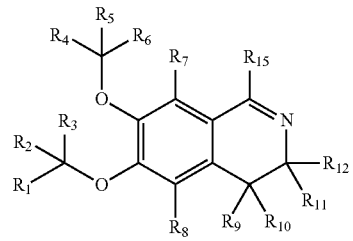

(VII)

comprising:
a first step of reacting a compound of Formula VI:

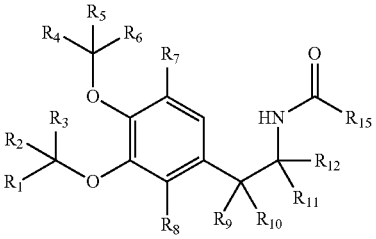

(VI)

with a dehydrating agent in a reaction solvent;
a second step of adding a quenching solvent and an antisolvent to the reaction mixture; and
a third step of isolating the salt of the compound of Formula VII from the reaction mixture;
wherein:
$R_1$-$R_{12}$ and $R_{15}$ are independently selected from the group consisting of hydrogen and deuterium.

In certain embodiments, said salt of the compound of Formula I is the hydrochloride salt.

In certain embodiments, said dehydrating agent is selected from the group consisting of phosphorous oxychloride, phosphorus pentachloride, and thionyl chloride.

In certain embodiments, the amount of said phosphorous oxychloride is between about 0.5 to about 4 molar equivalents relative to the compound of Formula VI.

In certain embodiments, the amount of said phosphorous oxychloride is between about 1.6 to about 2.0 molar equivalents relative to the compound of Formula VI.

In certain embodiments, the amount of said phosphorous oxychloride is about 1.8 molar equivalents relative to the compound of Formula VI.

In certain embodiments, said reaction solvent is selected from the group consisting of methyl tert-butyl ether, toluene, and acetonitrile.

In certain embodiments, said reaction solvent is acetonitrile.

In certain embodiments, the volume of said acetonitrile is between about 1 to about 4 times the mass of the compound of Formula VI.

In certain embodiments, the volume of said acetonitrile is between about 1.5 to about 2.5 times the mass of the compound of Formula VI.

In certain embodiments, the volume of said acetonitrile is about 2 times the mass of the compound of Formula VI.

In certain embodiments, said quenching solvent is anprotic solvents selected from the group consisting of water, an alcohol, and a protic acid.

In certain embodiments, said quenching solvent is selected from the group consisting of ethanol, 1-propanol, isopropanol, 1-butanol, 2-methylpropanol, tert-butanol, and 1-pentanol.

In certain embodiments, said quenching solvent is 1-butanol.

In certain embodiments, the amount of said 1-butanol is between about 2 to about 8 molar equivalents relative to the compound of Formula VI.

In certain embodiments, the amount of said 1-butanol is between about 2.4 to about 6 molar equivalents relative to the compound of Formula VI.

In certain embodiments, the amount of said 1-butanol is between about 3.4 to about 4.2 molar equivalents relative to the compound of Formula VI.

In certain embodiments, the amount of said 1-butanol is about 3.8 molar equivalents relative to the compound of Formula VI.

In certain embodiments, said quenching solvent is selected from the group consisting of hydrogen chloride, hydrogen bromide, hydrogen iodide, phosphoric acid, sulfuric acid, methanesulfonic acid, formic acid, acetic acid, and trifluoroacetic acid.

In certain embodiments, said antisolvent is selected from the group consisting of methyl tert-butyl ether, ethyl acetate, isopropyl acetate, 2-methyltetrahydrofuran, diethyl ether, toluene, hexane, pentane, and cyclohexane.

In certain embodiments, said antisolvent is methyl tert-butyl ether.

In certain embodiments, the volume of said methyl tert-butyl ether is between about 1 to about 10 times the mass of the compound of Formula VI.

In certain embodiments, the volume of said methyl tert-butyl ether is between about 3 to about 5 times the mass of the compound of Formula VI.

In certain embodiments, the volume of said methyl tert-butyl ether is about 4 times the mass of the compound of Formula VI.

In certain embodiments, said first reaction step is carried out at reflux.

In certain embodiments, said first reaction step is held at a temperature of between about 0° C. to about 100° C.

In certain embodiments, said first reaction step is held at a temperature of between about 75° C. to about 95° C.

In certain embodiments, said first reaction step is held at a temperature of between about 80° C. to about 85° C.

In certain embodiments, said first reaction step is held at a temperature of between about 80° C. to about 85° C. for about 2 hours.

In certain embodiments, after said first reaction step is heated to between about 80° C. to about 85° C., the reaction mixture is cooled to a temperature between about 25° C. to about 35° C.

In certain embodiments, said second reaction step is carried out at between about 0° C. to about 100° C.

In certain embodiments, said second reaction step is carried out at between about 10° C. to about 50° C.

In certain embodiments, said second reaction step is carried out at between about 25° C. to about 35° C.

In certain embodiments, the reaction mixture is held at a temperature between about 25° C. to about 35° C. for about 12 hours after the addition of said quenching solvent and said antisolvent.

In certain embodiments, said salt of the compound of Formula VII is isolated by filtration.

In certain embodiments, disclosed herein is a process of purifying a hydrochloride salt of a compound of Formula VII:

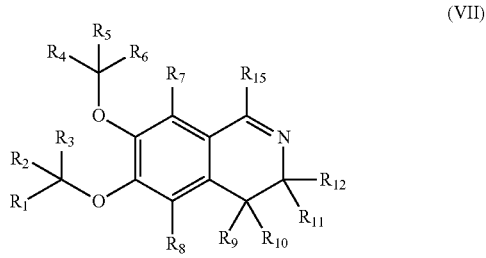

(VII)

comprising:

a first step of mixing the compound of Formula VII with one or more solvents; and a second step of filtering the salt of the compound of Formula VII from the mixture;

wherein:

$R_1$-$R_{12}$ and $R_{15}$ are independently selected from the group consisting of hydrogen and deuterium.

In certain embodiments, said solvent is selected from the group consisting of ethanol, 1-propanol, isopropanol, 2-methylpropanol, tert-butanol, 1-butanol, 1-pentanol, acetone, acetonitrile, ethyl acetate, methyl tert-butyl ether, hydrogen chloride, hydrogen bromide, hydrogen iodide, phosphoric acid, sulfuric acid, methanesulfonic acid, formic acid, acetic acid, and trifluoroacetic acid.

In certain embodiments, said solvent is a mixture of ethanol and methyl tert-butyl ether.

In certain embodiments, said solvent is a mixture of 10% ethanol and 90% methyl tert-butyl ether.

In certain embodiments, said first mixing step is carried out at between about 0° C. to about 60° C.

In certain embodiments, said first mixing step is carried out at between about 20° C. to about 40° C.

In certain embodiments, said first mixing step is carried out at between about 28° C. to about 32° C.

In certain embodiments, disclosed herein is a process of preparing a compound of Formula IX:

(IX)

$$\text{(structure IX with substituents } R_1\text{-}R_{27}\text{)}$$

comprising:
a step of reacting a compound of Formula VII or a salt thereof with a compound of Formula VIII in one or more solvents:

(VII)

$$\text{(structure VII)}$$

(VIII)

$$\text{(structure VIII with } X^\ominus\text{)}$$

wherein:
$R_1$-$R_{27}$ are independently selected from the group consisting of hydrogen and deuterium; and X is selected from the group consisting of halogen, alkyl sulfate, alkyl sulfonate, halosulfonate, perhaloalkyl sulfonate, aryl sulfonate, alkylaryl sulfonate, dialkyloxonium, alkylphosphate, and alkylcarbonate, any of which may be optionally substituted.

In certain embodiments, said solvent is selected from the group consisting of water, methanol, and ethanol.

In certain embodiments, said solvent is a mixture of methanol and water.

In certain embodiments, said methanol and water mixture is between about five parts methanol to one part water and about one part methanol to one part water.

In certain embodiments, said methanol and water mixture is between about four parts methanol to one part water and about two parts methanol to one part water.

In certain embodiments, said methanol and water mixture is about three parts methanol to one part water.

In certain embodiments, the volume of said mixture of methanol and water is between about 2 and about 10 times the mass of the compound of Formula VII.

In certain embodiments, the volume of said mixture of methanol and water is between about 4 and about 8 times the mass of the compound of Formula VII.

In certain embodiments, the volume of said mixture of methanol and water is about 6 times the mass of the compound of Formula VII.

In certain embodiments, said solvent is a mixture of ethanol and water.

In certain embodiments, said ethanol and water mixture is between about five parts ethanol to one part water and about one part ethanol to one part water.

In certain embodiments, said ethanol and water mixture is between about four parts ethanol to one part water and about two parts ethanol to one part water.

In certain embodiments, said ethanol and water mixture is about three parts ethanol to one part water.

In certain embodiments, the volume of said mixture of ethanol and water is between about 2 and about 10 times the mass of the compound of Formula VII.

In certain embodiments, the volume of said mixture of ethanol and water is between about 4 and about 8 times the mass of the compound of Formula VII.

In certain embodiments, the volume of said mixture of ethanol and water is about 6 times the mass of the compound of Formula VII.

In certain embodiments, said reaction step is held at a temperature of between about 0° C. to about 100° C.

In certain embodiments, said reaction step is held at a temperature of between about 25° C. to about 70° C.

In certain embodiments, said reaction step is held at a temperature of between about 40° C. to about 60° C.

In certain embodiments, said reaction step is held at a temperature of between about 45° C. to about 50° C.

In certain embodiments, said reaction step is carried out for about 1 to about 96 hours.

In certain embodiments, said reaction step is carried out for about 24 to about 72 hours.

In certain embodiments, said reaction step is carried out for about 48 hours.

In certain embodiments, wherein the compound of Formula VII is the hydrochloride salt and a base is added during the reaction step.

In certain embodiments, said base is selected from the group consisting of alkali metal carbonates, alkali metal bicarbonates, alkali metal alkoxides, alkali metal hydroxides, alkali metal hydrides, and trialkylamines.

In certain embodiments, said base is an alkali metal carbonate.

In certain embodiments, said base is potassium carbonate.

In certain embodiments, disclosed herein is a process of preparing a compound of Formula XI:

(XI)

$$\text{(structure XI)}$$

comprising:
a first step of reacting a compound of Formula X or a salt thereof with a base in one or more solvents:

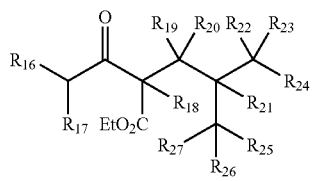

(X)

a second step of adjusting the pH of the reaction mixture by addition of an acid;

a third step of adding dimethylamine or a salt thereof and a formaldehyde equivalent to the reaction mixture;

a fourth step of lowering the pH of the reaction mixture by addition of an acid;

a fifth step of raising the pH of the reaction mixture by addition of an base;

a sixth step of adding dimethylamine or a salt thereof to the reaction mixture;

wherein:

$R_{16}$-$R_{27}$ are independently selected from the group consisting of hydrogen and deuterium.

In certain embodiments, the base used in the first hydrolysis step or the fifth pH adjustment step is selected from the group consisting of alkali metal carbonates and alkali metal hydroxides.

In certain embodiments, said base is an alkali metal hydroxide.

In certain embodiments, said base is potassium hydroxide.

In certain embodiments, said dimethylamine is dimethylamine hydrochloride.

In certain embodiments, said formaldehyde equivalent is selected from the group consisting of formaldehyde, aqueous formaldehyde solution, paraformaldehyde, and trioxane.

In certain embodiments, said formaldehyde equivalent is aqueous formaldehyde solution.

In certain embodiments, the acid used in the second pH adjustment step or the fourth pH adjustment step is selected from the group consisting of hydrochloric acid, sulfuric acid, phosphoric acid, and methanesulfonic acid.

In certain embodiments, said acid is hydrochloric acid.

In certain embodiments, a phase transfer catalyst is added during the third reaction step.

In certain embodiments, said phase transfer catalyst is tetrabutylammonium bromide.

In certain embodiments, the amount of said tetrabutylammonium bromide is about 0.1 molar equivalents relative to said compound of Formula X.

In certain embodiments, said solvent is water.

In certain embodiments, the first hydrolysis step is carried out by the addition of about 1 to about 2 molar equivalents of potassium hydroxide relative to said compound of Formula X.

In certain embodiments, the first hydrolysis step is carried out by the addition of about 1 to about 1.2 molar equivalents of potassium hydroxide relative to said compound of Formula X.

In certain embodiments, the first hydrolysis step is carried out by the addition of about 1.1 molar equivalents of potassium hydroxide relative to said compound of Formula X.

In certain embodiments, the first hydrolysis step is carried out at a temperature of between about 0° C. to about 100° C.

In certain embodiments, the first hydrolysis step is carried out at a temperature of between about 20° C. to about 40° C.

In certain embodiments, the second pH adjustment step results in a pH of about 6 to about 8.

In certain embodiments, the second pH adjustment step results in a pH of about 6.8 to about 7.2.

In certain embodiments, the second pH adjustment step is carried out at a temperature of between about 10° C. to about 60° C.

In certain embodiments, the third addition step is carried out by the addition of about 1 to about 2 molar equivalents of dimethylamine and formaldehyde equivalents relative to said compound of Formula X.

In certain embodiments, the third addition step is carried out by the addition of about 1.25 to about 1.75 molar equivalents of dimethylamine and about 1.25 to about 1.75 molar equivalents of formaldehyde equivalents relative to said compound of Formula X.

In certain embodiments, the third addition step is carried out by the addition of about 1.5 molar equivalents of dimethylamine and about 1.68 molar equivalents of formaldehyde equivalents relative to said compound of Formula X.

In certain embodiments, the third addition step is carried out at a temperature of between about 10° C. to about 60° C.

In certain embodiments, the third addition step is carried out at a temperature of between about 25° C. to about 35° C.

In certain embodiments, the reaction temperature is maintained for about 1 to about 24 hours after third addition step.

In certain embodiments, the reaction temperature is maintained for about 9 to about 15 hours after third addition step.

In certain embodiments, the reaction temperature is maintained for about 12 hours after third addition step.

In certain embodiments, the fourth pH adjustment step results in a pH of less than 3.

In certain embodiments, the fourth pH adjustment step results in a pH of less than 1.

In certain embodiments, the fourth pH adjustment step is carried out at a temperature of between about 10° C. to about 60° C.

In certain embodiments, the fourth pH adjustment step is carried out at a temperature of between about 25° C. to about 35° C.

In certain embodiments, the fifth pH adjustment step results in a pH of greater than 10.

In certain embodiments, the fifth pH adjustment step results in a pH of about 12 to about 13.

In certain embodiments, the fifth pH adjustment step is carried out at a temperature of between about 10° C. to about 60° C.

In certain embodiments, the fifth pH adjustment step is carried out at a temperature of between about 25° C. to about 35° C.

In certain embodiments, the sixth addition step is carried out by the addition of about 1 to about 2 molar equivalents of dimethylamine relative to said compound of Formula X.

In certain embodiments, the sixth addition step is carried out by the addition of about 1.25 to about 1.75 molar equivalents of dimethylamine relative to said compound of Formula X.

In certain embodiments, the sixth addition step is carried out by the addition of about 1.5 molar equivalents of dimethylamine relative to said compound of Formula X.

In certain embodiments, the sixth addition step is carried out at a temperature of between about 10° C. to about 60° C.

In certain embodiments, the sixth addition step is carried out at a temperature of between about 25° C. to about 35° C.

In certain embodiments, the reaction temperature is maintained for about 1 to about 96 hours after third addition step.

In certain embodiments, the reaction temperature is maintained for about 24 to about 48 hours after third addition step.

In certain embodiments, the reaction temperature is maintained for about 36 hours after third addition step.

The compounds as disclosed herein may also contain less prevalent isotopes for other elements, including, but not limited to, $^{13}C$ or $^{14}C$ for carbon, $^{33}S$, $^{34}S$, or $^{36}S$ for sulfur, $^{15}N$ for nitrogen, and $^{17}O$ or $^{18}O$ for oxygen.

All publications and references cited herein are expressly incorporated herein by reference in their entirety. However, with respect to any similar or identical terms found in both the incorporated publications or references and those explicitly put forth or defined in this document, then those terms definitions or meanings explicitly put forth in this document shall control in all respects.

As used herein, the terms below have the meanings indicated.

The singular forms "a," "an," and "the" may refer to plural articles unless specifically stated otherwise.

The term "about," as used herein, is intended to qualify the numerical values which it modifies, denoting such a value as variable within a margin of error. When no particular margin of error, such as a standard deviation to a mean value given in a chart or table of data, is recited, the term "about" should be understood to mean that range which would encompass the recited value and the range which would be included by rounding up or down to that figure as well, taking into account significant figures.

When ranges of values are disclosed, and the notation "from $n_1$ . . . to $n_2$" or "$n_1$-$n_2$" is used, where $n_1$ and $n_2$ are the numbers, then unless otherwise specified, this notation is intended to include the numbers themselves and the range between them. This range may be integral or continuous between and including the end values.

The term "deuterium enrichment" refers to the percentage of incorporation of deuterium at a given position in a molecule in the place of hydrogen. For example, deuterium enrichment of 1% at a given position means that 1% of molecules in a given sample contain deuterium at the specified position. Because the naturally occurring distribution of deuterium is about 0.0156%, deuterium enrichment at any position in a compound synthesized using non-enriched starting materials is about 0.0156%. The deuterium enrichment can be determined using conventional analytical methods known to one of ordinary skill in the art, including mass spectrometry and nuclear magnetic resonance spectroscopy.

The term "is/are deuterium," when used to describe a given position in a molecule such as $R_1$-$R_{27}$ or the symbol "D", when used to represent a given position in a drawing of a molecular structure, means that the specified position is enriched with deuterium above the naturally occurring distribution of deuterium. In one embodiment deuterium enrichment is no less than about 1%, in another no less than about 5%, in another no less than about 10%, in another no less than about 20%, in another no less than about 50%, in another no less than about 70%, in another no less than about 80%, in another no less than about 90%, or in another no less than about 98% of deuterium at the specified position.

The term "isotopic enrichment" refers to the percentage of incorporation of a less prevalent isotope of an element at a given position in a molecule in the place of the more prevalent isotope of the element.

The term "non-isotopically enriched" refers to a molecule in which the percentages of the various isotopes are substantially the same as the naturally occurring percentages.

Asymmetric centers exist in the compounds disclosed herein. These centers are designated by the symbols "R" or "S," depending on the configuration of substituents around the chiral carbon atom. It should be understood that the invention encompasses all stereochemical isomeric forms, including diastereomeric, enantiomeric, and epimeric forms, as well as D-isomers and L-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds disclosed herein may exist as geometric isomers. The present invention includes all cis, trans, syn, anti, entgegen (E), and zusammen (Z) isomers as well as the appropriate mixtures thereof. Additionally, compounds may exist as tautomers; all tautomeric isomers are provided by this invention. Additionally, the compounds disclosed herein can exist in unsolvated as well as solvated forms with pharmaceutically acceptable solvents such as water, ethanol, and the like. In general, the solvated forms are considered equivalent to the unsolvated forms.

The terms "3S,11bS enantiomer" or the term "3R,11bR enantiomer" refers to either of the $d_6$-tetrabenazine stereoisomers having the structural formulas shown below:

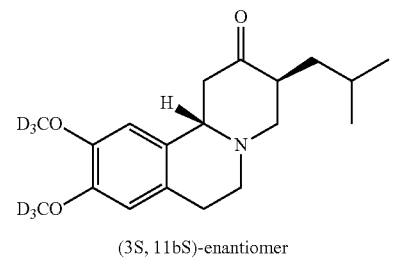

(3S, 11bS)-enantiomer

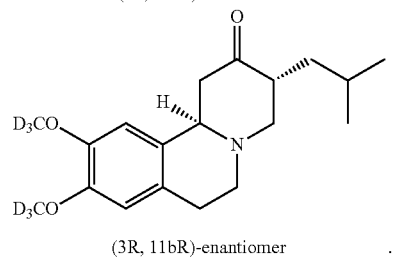

(3R, 11bR)-enantiomer

In certain embodiments, a chemical structure may be drawn as either the 3S,11bS enantiomer or the 3R,11bR enantiomer, but the text of the specification may indicate that the 3S,11bS enantiomer, the 3R,11bR enantiomer, a racemic mixture thereof (which may be described as (RR, SS)-d6-tetrabenazine), or all of the foregoing may be intended to be described.

The terms "(3S, 11bS)-enantiomer" or "(3R, 11bR)-enantiomer" or the as applied to a compound of Formula I refers to either of the stereoisomers of compounds of Formula I shown below:

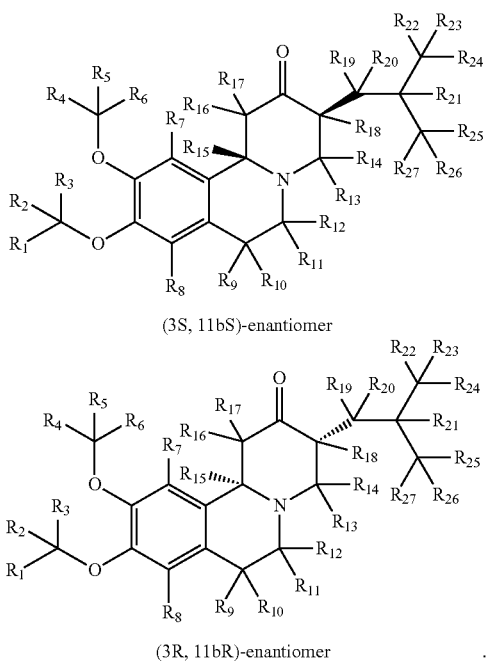

(3S, 11bS)-enantiomer (3R, 11bR)-enantiomer

The term "bond" refers to a covalent linkage between two atoms, or two moieties when the atoms joined by the bond are considered to be part of larger substructure. A bond may be single, double, or triple unless otherwise specified. A dashed line between two atoms in a drawing of a molecule indicates that an additional bond may be present or absent at that position.

The term "alkoxy," as used herein, alone or in combination, refers to an alkyl ether radical, wherein the term alkyl is as defined below. Examples of suitable alkyl ether radicals include methoxy, ethoxy, n-propoxy, isopropoxy, n-butoxy, iso-butoxy, sec-butoxy, tert-butoxy, and the like.

The term "alkyl," as used herein, alone or in combination, refers to a straight-chain or branched-chain alkyl radical containing from 1 to 20 carbon atoms. In certain embodiments, said alkyl will comprise from 1 to 10 carbon atoms. In further embodiments, said alkyl will comprise from 1 to 6 carbon atoms. Alkyl groups may be optionally substituted as defined herein. Examples of alkyl radicals include methyl, ethyl, n-propyl, isopropyl, n-butyl, isobutyl, sec-butyl, tert-butyl, pentyl, iso-amyl, hexyl, octyl, noyl and the like. The term "alkylene," as used herein, alone or in combination, refers to a saturated aliphatic group derived from a straight or branched chain saturated hydrocarbon attached at two or more positions, such as methylene (—CH$_2$—). Unless otherwise specified, the term "alkyl" may include "alkylene" groups.

The term "alkylamino," as used herein, alone or in combination, refers to an alkyl group attached to the parent molecular moiety through an amino group. Suitable alkylamino groups may be mono- or dialkylated, forming groups such as, for example, N-methylamino, N-ethylamino, N,N-dimethylamino, N,N-ethylmethylamino and the like.

The term "amino," as used herein, alone or in combination, refers to —NRR', wherein R and R' are independently selected from the group consisting of hydrogen, alkyl, acyl, heteroalkyl, aryl, cycloalkyl, heteroaryl, and heterocycloalkyl, any of which may themselves be optionally substituted. Additionally, R and R' may combine to form heterocycloalkyl, either of which may be optionally substituted.

The term "aryl," as used herein, alone or in combination, means a carbocyclic aromatic system containing one, two or three rings wherein such polycyclic ring systems are fused together. The term "aryl" embraces aromatic groups such as phenyl, naphthyl, anthracenyl, and phenanthryl.

The term "halo," or "halogen," as used herein, alone or in combination, refers to fluorine, chlorine, bromine, or iodine.

The term "haloalkoxy," as used herein, alone or in combination, refers to a haloalkyl group attached to the parent molecular moiety through an oxygen atom.

The term "haloalkyl," as used herein, alone or in combination, refers to an alkyl radical having the meaning as defined above wherein one or more hydrogens are replaced with a halogen. Specifically embraced are monohaloalkyl, dihaloalkyl and polyhaloalkyl radicals. A monohaloalkyl radical, for one example, may have an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Haloalkylene" refers to a haloalkyl group attached at two or more positions. Examples include fluoromethylene (—CFH—), difluoromethylene (—CF$_2$—), chloromethylene (—CHC$_1$—) and the like.

The term "perhaloalkoxy" refers to an alkoxy group where all of the hydrogen atoms are replaced by halogen atoms.

The term "perhaloalkyl" as used herein, alone or in combination, refers to an alkyl group where all of the hydrogen atoms are replaced by halogen atoms.

The terms "sulfonate," "sulfonic acid," and "sulfonic," as used herein, alone or in combination, refer the —SO$_3$H group and its anion or the —SO$_3$— group.

The terms "sulfate," "sulfuric acid," and "sulfuric," as used herein, alone or in combination, refer the HOS(=O)$_2$OH group and its mono- or dianion or the —SO$_4$— group.

The terms "phosphate," "phosphoric acid," and "phosphoric," as used herein, alone or in combination, refer the P(=O)(OH)$_3$ group and its mono-, di, or trianion or the —PO$_4$— group.

The terms "carbonate," as used herein, alone or in combination, refer the —OC(=O)O— group.

The term "VMAT2" refers to vesicular monoamine transporter 2, an integral membrane protein that acts to transport monoamines—particularly neurotransmitters such as dopamine, norepinephrine, serotonin, and histamine—from cellular cytosol into synaptic vesicles.

The term "VMAT2-mediated disorder," refers to a disorder that is characterized by abnormal VMAT2 activity. A VMAT2-mediated disorder may be completely or partially mediated by modulating VMAT2. In particular, a VMAT2-mediated disorder is one in which inhibition of VMAT2 results in some effect on the underlying disorder e.g., administration of a VMAT2 inhibitor results in some improvement in at least some of the patients being treated.

The term "VMAT2 inhibitor", "inhibit VMAT2", or "inhibition of VMAT2" refers to the ability of a compound disclosed herein to alter the function of VMAT2. A VMAT2 inhibitor may block or reduce the activity of VMAT2 by forming a reversible or irreversible covalent bond between the inhibitor and VMAT2 or through formation of a noncovalently bound complex. Such inhibition may be manifest only in particular cell types or may be contingent on a particular biological event. The term "VMAT2 inhibitor", "inhibit VMAT2", or "inhibition of VMAT2" also refers to altering the function of VMAT2 by decreasing the probability that a complex forms between a VMAT2 and a natural substrate VMAT2-mediated disorders include, but are not limited to chronic hyperkinetic movement disorders, which can be psychogenic (e.g., tics), idiopathic (as in, e.g., Tourette's syndrome and Parkinson's Disease, genetic (as in, e.g., the chorea characteristic of Huntington's Disease), infectious (as in, e.g., Sydenham's Chorea), or, drug induced, as in tardive dyskinesia. Unless otherwise stated, "chronic hyperkinetic movement disorders" refers to and includes all psychogenic, idiopathic, genetic, and drug-induced movement disorders. VMAT2 disorders also include disoders such as oppositional defiant disorder.

The compounds disclosed herein can exist as therapeutically acceptable salts. The term "therapeutically acceptable salt," as used herein, represents salts or zwitterionic forms of the compounds disclosed herein which are therapeutically acceptable as defined herein. The salts can be prepared during the final isolation and purification of the compounds or separately by reacting the appropriate compound with a suitable acid or base. Therapeutically acceptable salts include acid and basic addition salts. For a more complete discussion of the preparation and selection of salts, refer to "Handbook of Pharmaceutical Salts, Properties, and Use," Stah and Wermuth, Ed., (Wiley-VCH and VHCA, Zurich, 2002) and Berge et al., *J. Pharm. Sci.* 1977, 66, 1-19.

Suitable acids for use in the preparation of pharmaceutically acceptable salts include, but are not limited to, acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, boric acid, (+)-camphoric acid, camphorsulfonic acid, (+)-(1S)-camphor-10-sulfonic acid, capric acid, caproic acid, caprylic acid, cinnamic acid, citric acid, cyclamic acid, cyclohexanesulfamic acid, dodecyl sulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucuronic acid, L-glutamic acid, α-oxo-glutaric acid, glycolic acid, hippuric acid, hydrobromic acid, hydrochloric acid, hydroiodic acid, (+)-L-lactic acid, (±)-DL-lactic acid, lactobionic acid, lauric acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, perchloric acid, phosphoric acid, L-pyroglutamic acid, saccharic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid, undecylenic acid, and valeric acid.

Suitable bases for use in the preparation of pharmaceutically acceptable salts, including, but not limited to, inorganic bases, such as magnesium hydroxide, calcium hydroxide, potassium hydroxide, zinc hydroxide, or sodium hydroxide; and organic bases, such as primary, secondary, tertiary, and quaternary, aliphatic and aromatic amines, including L-arginine, benethamine, benzathine, choline, deanol, diethanolamine, diethylamine, dimethylamine, dipropylamine, diisopropylamine, 2-(diethylamino)-ethanol, ethanolamine, ethylamine, ethylenediamine, isopropylamine, N-methylglucamine, hydrabamine, 1H-imidazole, L-lysine, morpholine, 4-(2-hydroxyethyl)-morpholine, methylamine, piperidine, piperazine, propylamine, pyrrolidine, 1-(2-hydroxyethyl)-pyrrolidine, pyridine, quinuclidine, quinoline, isoquinoline, secondary amines, triethanolamine, trimethylamine, triethylamine, N-methyl-D-glucamine, 2-amino-2-(hydroxymethyl)-1,3-propanediol, and tromethamine.

While it may be possible for the compounds of the subject invention to be administered as the raw chemical, it is also possible to present them as a pharmaceutical composition. Accordingly, provided herein are pharmaceutical compositions which comprise one or more of certain compounds disclosed herein, or one or more pharmaceutically acceptable salts, prodrugs, or solvates thereof, together with one or more pharmaceutically acceptable carriers thereof and optionally one or more other therapeutic ingredients. Proper formulation is dependent upon the route of administration chosen. Any of the well-known techniques, carriers, and excipients may be used as suitable and as understood in the art; e.g., in Remington's Pharmaceutical Sciences. The pharmaceutical compositions disclosed herein may be manufactured in any manner known in the art, e.g., by means of conventional mixing, dissolving, granulating, dragee-making, levigating, emulsifying, encapsulating, entrapping or compression processes. The pharmaceutical compositions may also be formulated as a modified release dosage form, including delayed-, extended-, prolonged-, sustained-, pulsatile-, controlled-, accelerated- and fast-, targeted-, programmed-release, and gastric retention dosage forms. These dosage forms can be prepared according to conventional methods and techniques known to those skilled in the art (see, Remington: The Science and Practice of Pharmacy, supra; Modified-Release Drug Deliver Technology, Rathbone et al., Eds., Drugs and the Pharmaceutical Science, Marcel Dekker, Inc., New York, N.Y., 2002; Vol. 126).

General Synthetic Methods for Preparing Compounds

Isotopic hydrogen can be introduced into a compound as disclosed herein by synthetic techniques that employ deuterated reagents, whereby incorporation rates are pre-determined; and/or by exchange techniques, wherein incorporation rates are determined by equilibrium conditions, and may be highly variable depending on the reaction conditions. Synthetic techniques, where tritium or deuterium is directly and specifically inserted by tritiated or deuterated reagents of known isotopic content, may yield high tritium or deuterium abundance, but can be limited by the chemistry required. Exchange techniques, on the other hand, may yield lower tritium or deuterium incorporation, often with the isotope being distributed over many sites on the molecule.

The compounds as disclosed herein can be prepared by methods known to one of skill in the art and routine modifications thereof, and/or following procedures similar to those described in the Example section herein and routine modifications thereof, and/or procedures found in WO 2005077946; WO 2008/058261; EP 1716145; Lee et al., *J. Med. Chem.*, 1996, (39), 191-196; Kilbourn et al., *Chirality*, 1997, (9), 59-62; Boldt et al., *Synth. Commun.*, 2009, (39), 3574-3585; Rishel et al., *J. Org. Chem.*, 2009, (74), 4001-4004; DaSilva et al., *Appl. Radiat. Isot.*, 1993, 44(4), 673-676; Popp et al., *J. Pharm. Sci.*, 1978, 67(6), 871-873; Ivanov et al., *Heterocycles* 2001, 55(8), 1569-1572; U.S. Pat. Nos. 2,830,993; 3,045,021; WO 2007130365; WO 2008058261, which are hereby incorporated in their entirety, and references cited therein and routine modifications thereof. Compounds as disclosed herein can also be prepared as shown in any of the following schemes and routine modifications thereof.

The following schemes can be used to practice the present invention. Any position shown as hydrogen may optionally be replaced with deuterium.

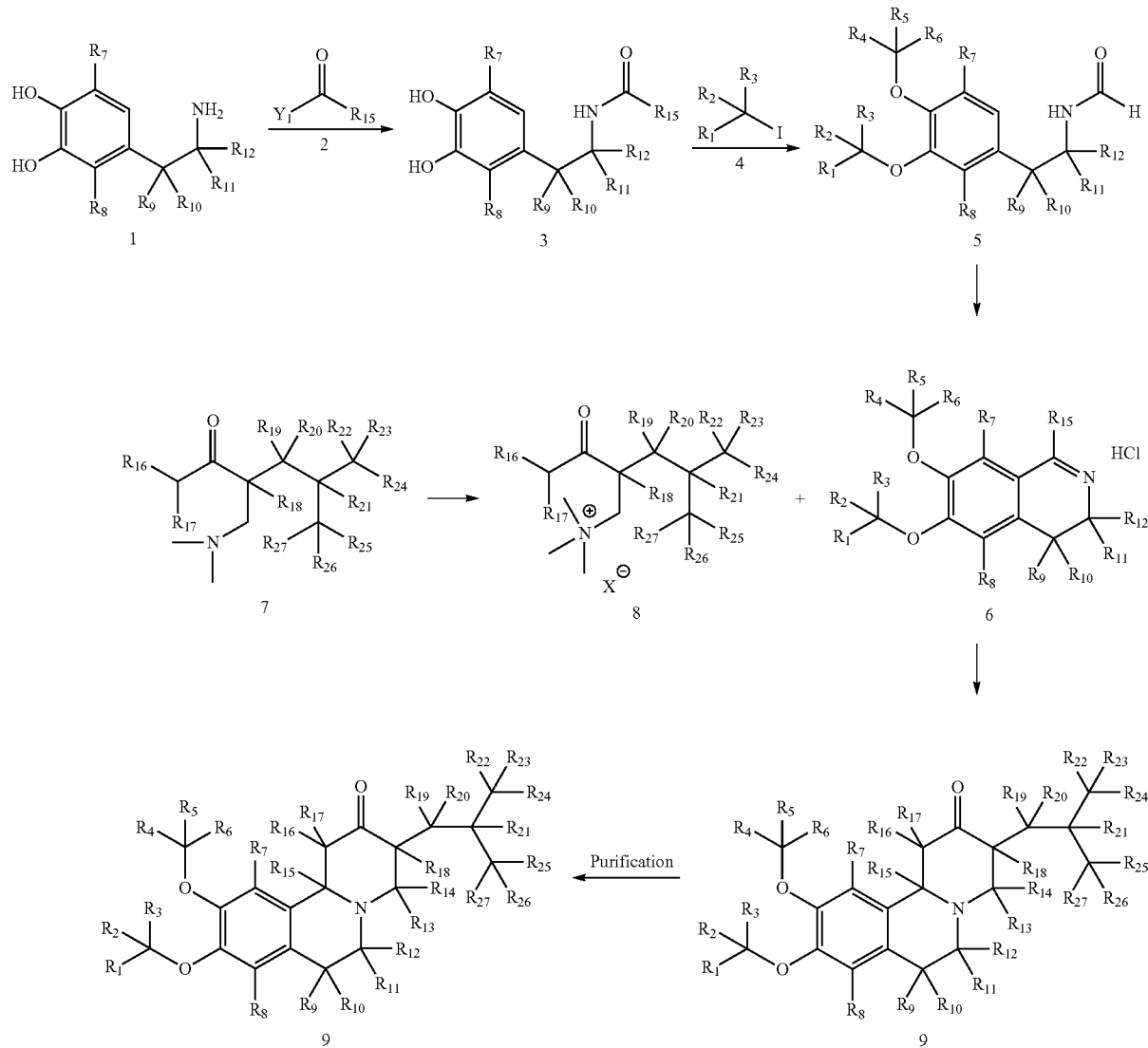

Compound 1 is reacted with compound 2, wherein $Y_1$ is selected from the group consisting of acetoxy, alkoxy, halogen, haloalkoxy, perhaloalkoxy, heteroalkoxy, and aryloxy, any of which may be optionally substituted, in the presence of an appropriate basic catalyst, such as sodium tert-butoxide, at an elevated temperature to give compound 3. Compound 3 is reacted with compound 4 in the presence of an appropriate base, such as potassium carbonate, in an appropriate solvent, such as acetone, to afford compound 5. Compound 5 is reacted with an appropriate dehydrating agent, such as phosphorous oxychloride, in an appropriate solvent, such as acetonitrile, at an elevated temperature to give compound 6. Compound 7 is reacted with an appropriate methylating agent, such as methyl iodide, in an appropriate solvent, such as methyl tert-butyl ether, at an elevated temperature to give compound 8. Compound 6 is reacted with compound 8, in the presence of an appropriate base, such as potassium carbonate, in an appropriate solvent, such as a mixture of methanol and water, at an elevated temperature to afford compound 9 of Formula I. Compound 9 may be optionally purified by recrystallization from an appropriate solvent, such as ethanol.

Deuterium can be incorporated to different positions synthetically, according to the synthetic procedures as shown in Scheme I, by using appropriate deuterated intermediates. For example, to introduce deuterium at one or more positions of $R_7$-$R_{12}$, compound 1 with the corresponding deuterium substitutions can be used. To introduce deuterium at $R_{15}$, compound 2 with the corresponding deuterium substitution can be used. To introduce deuterium at one or more positions of $R_1$-$R_6$, compound 4 with the corresponding deuterium substitutions can be used. To introduce deuterium at one or more positions of $R_{16}$-$R_{29}$, compound 7 with the corresponding deuterium substitutions can be used.

Deuterium can also be incorporated to various positions having an exchangeable proton, via proton-deuterium equilibrium exchange.

Scheme II

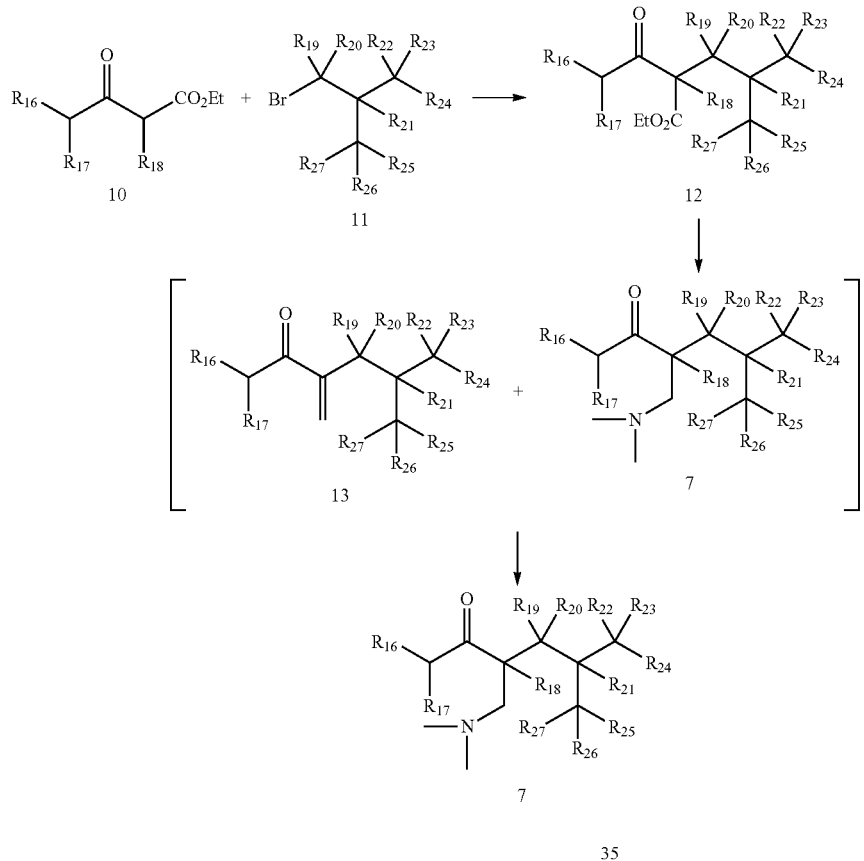

Compound 10 is reacted with compound 11, in the presence of an appropriate base, such as potassium carbonate, an optional alkylation catalyst, such as potassium iodide, and an optional phase transfer catalyst, such as tetrabutylammonium bromide, in an appropriate solvent, such as dimethylformamide, at an elevated temperature to give compound 12. Compound 12 is reacted with an appropriate base, such as potassium hydroxide, in an appropriate solvent, such as water, to afford an intermediate carboxylic acid which is further reacted with an appropriate secondary amine or salt thereof, such as dimethylamine hydrochloride, and an appropriate formaldehyde equivalent, such as aqueous formaldehyde solution, in the presence of an appropriate acid, such as hydrochloric acid, and an optional phase transfer catalyst, such as tetrabutylammonium bromide, to give a mixture of compound 7 and compound 13. The mixture of compound 7 and compound 13 is further reacted with an appropriate secondary amine or salt thereof, such as dimethylamine hydrochloride, in the presence of an appropriate base, such as potassium hydroxide, in an appropriate solvent, such as water, to give compound 7.

Deuterium can be incorporated to different positions synthetically, according to the synthetic procedures as shown in Scheme I, by using appropriate deuterated intermediates. For example, to introduce deuterium at one or more positions of $R_{16}$-$R_{18}$, compound 10 with the corresponding deuterium substitutions can be used. To introduce deuterium at one or more positions of $R_{19}$-$R_{27}$, compound 11 with the corresponding deuterium substitutions can be used.

Deuterium can also be incorporated to various positions having an exchangeable proton, via proton-deuterium equilibrium exchange.

The invention is further illustrated by the following examples. All IUPAC names were generated using CambridgeSoft's ChemDraw 13.0.

EXAMPLE 1

N-(2-(3,4-dihydroxy-phenyl)-ethyl)-formamide

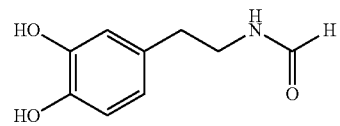 [SMILES: O=CNCCc1ccc(O)c(O)c1]

Step 1

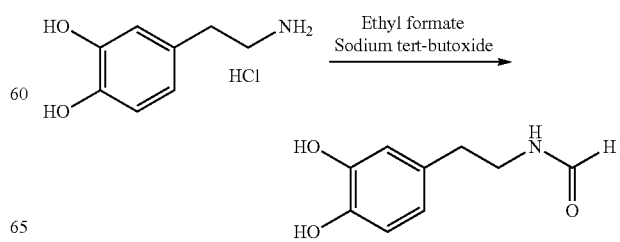

Optimization of Reaction Conditions

General Procedure:

Dopamine hydrochloride is suspended in ethyl formate at 25-30° C. The suspension is cooled to 10-15° C. and sodium tert-butoxide is added portionwise maintaining the same temperature. The reaction mixture is warmed to 50-55° C. for 12 hours. After completion of the reaction, ethanol is added to the reaction mass and the temperature is maintained for 2 hours. The reaction mass is filtered and washed with 2 volumes of ethanol. The filtrate is concentrated under vacuum and water (0.5 volumes) is added to the residue and stirred for 1 hour at 25-30° C. The solid is filtered and washed with water (0.25 volumes) and dried in an hot air oven at 55-60° C. for 8 hours.

TABLE 1

Optimization of reaction conditions by varying equivalents of sodium tert-butoxide

| Exp. No. | Batch Size | Reaction Conditions | Product Quantity | Product Yield | HPLC Purity |
|---|---|---|---|---|---|
| 1 | 250 g | Ethyl formate (10 eq) Sodium tert-butoxide (2 eq) Ethanol (5 vol) 50-55° C., 12 hours | 151 g | 63% | 98.2% |
| 2 | 250 g | Ethyl formate (10 eq) Sodium tert-butoxide (1.6 eq) Ethanol (5 vol) 50-55° C., 12 hours | 175 g | 73% | 92.7% |
| 3 | 50 g | Ethyl formate (10 eq) Sodium tert-butoxide (1.3 eq) Ethanol (5 vol) 50-55° C., 12 hours | 18.5 g | 38% | 96.8% |
| 4 | 50 g | Ethyl formate (10 eq) Sodium tert-butoxide (1.8 eq) Ethanol (5 vol) 50-55° C., 12 hours | 32.6 g | 68% | 94.4% |

Representative Example—Step 1

N-(2-(3,4-dihydroxy-phenyl)-ethyl)-formamide

Dopamine hydrochloride (250.0 g, 1.323 mol, 1.0 eq) was suspended in ethyl formate (2.5 L, 10.0 vol) at 25-30° C. The suspension was cooled to 10-15° C. and sodium tert-butoxide (202 g, 2.12 mol, 1.60 eq) was added portionwise maintaining the same temperature. The reaction mixture was warmed to 55-60° C. for 12 hours and then concentrated under reduced pressure. To the remaining residue, water (125 mL, 0.5 vol) was added and stirred for 15 minutes. The volatile organic solvents were distilled under vacuum whereupon the product precipitated. The suspension was cooled to 25-30° C. and purified water (500 mL, 2.0 vol) was added. The solid was filtered and washed with water (125 mL, 0.5 vol) and dried in an oven at 55-60° C. for 8 hours to afford the title compound as a brown powder (203 g, yield=84.5%). $^1$H NMR (300 MHz, CDCl$_3$), δ 8.72 (s, broad, 2H), 7.96 (s, 1H), 6.548-6.630 (dd, 2H, J=8.1), 6.407-6.441 (d, 1H, J=2.1), 3.169-3.237 (q, 2H, J=6.9), 2.485-2.535 (t, 2H, J=7.8); LC-MS: m/z=181.92 (MH)$^+$.

EXAMPLE 2 d$_6$-6,7-Dimethoxy-3,4-dihydroisoquinoline hydrochloride

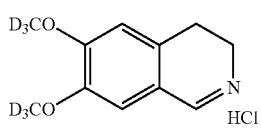

Step 1

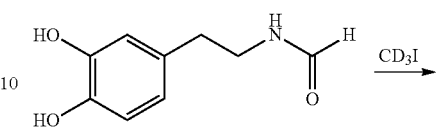

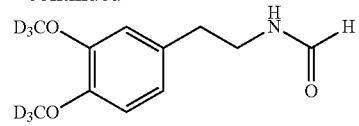

Optimization of Reaction Conditions

General Procedure:

N-(2-(3,4-dihydroxy-phenyl)-ethyl)-formamide is charged with solvent, base, phase transfer catalyst if any, and d$_3$-methyl iodide (CD$_3$I) at 25-30° C. The reaction temperature is set and maintained for the specified time. The reaction is filtered, the filtrate distilled under reduced pressure, and the crude product partitioned between dichloromethane (6.0 vol) and water (4.0 vol). The layers are separated and the organic layer is washed twice with 3% aqueous NaOH solution (2×4.0 vol) followed by water (4.0 vol). The organic layer is distilled under reduced pressure to give crude d$_6$-N-(2-(3,4-dimethoxy-phenyl)-ethyl)-formamide.

TABLE 2

Optimization of reaction conditions by varying solvent

| Exp. No. | Batch Size | Reaction Conditions | Product Quantity | Product Yield | HPLC Purity |
|---|---|---|---|---|---|
| 1 | 50 g | K$_2$CO$_3$ (3 eq) CH$_3$I (2.2 eq) Acetone (8 vol) | 50 g | 86.6% | 93.9% |

TABLE 2-continued

Optimization of reaction conditions by varying solvent

| Exp. No. | Batch Size | Reaction Conditions | Product Quantity | Product Yield | HPLC Purity |
|---|---|---|---|---|---|
| | | Tetrabutylammonium bromide (0.05 eq) 38-42° C., 36 hours | | | |
| 2 | 25 g | K$_2$CO$_3$ (3 eq) CH$_3$I (2.2 eq) Acetonitrile (8 vol) Tetrabutylammonium bromide (0.05 eq) 38-42° C., 36 hours | 21 g | 75% | — |
| 3 | 50 g | K$_2$CO$_3$ (3 eq) CH$_3$I (2.2 eq) 2-Methyl-tetrahdrofuran (8 vol) Tetrabutylammonium bromide (0.05 eq) 38-42° C., 36 hours | Not isolated | — | — |

TABLE 3

Optimization of reaction conditions by varying solvent volume

| Exp. No. | Batch Size | Reaction Conditions | Product Quantity | Product Yield | HPLC Purity |
|---|---|---|---|---|---|
| 1 | 20 g | K$_2$CO$_3$ (3 eq) CH$_3$I (3 eq) Acetone (6 vol) 18-crown-6 (0.05 eq) 38-42° C., 12 hours | 22 g | 95.3% | — |
| 2 | 100 g | K$_2$CO$_3$ (3 eq) CH$_3$I (3 eq) Acetone (8 vol) 18-crown-6 (0.05 eq) 38-42° C., 12 hours | 116 g | ~100% | 92.4% |

TABLE 4

Optimization of reaction conditions by varying molar equivalents of methyl iodide

| Exp. No. | Batch Size | Reaction Conditions | Product Quantity | Product Yield | HPLC Purity |
|---|---|---|---|---|---|
| 1 | 50 g | K$_2$CO$_3$ (3 eq) CH$_3$I (2.2 eq) Acetone (8 vol) 28-35° C., 36 hours | 44.3 g | 76.7% | 94.2% |
| 2 | 50 g | K$_2$CO$_3$ (3 eq) CH$_3$I (2.4 eq) Acetone (8 vol) 28-35° C., 36 hours | 47.6 g | 82.4% | 90.9% |
| 3 | 50 g | K$_2$CO$_3$ (3 eq) CH$_3$I (2.6 eq) Acetone (8 vol) 28-35° C., 36 hours | 48 g | 83.0% | 93.5% |

TABLE 5

Optimization of reaction conditions by varying reaction temperature

| Exp. No. | Batch Size | Reaction Conditions | Product Quantity | Product Yield | HPLC Purity |
|---|---|---|---|---|---|
| 1 | 200 g | K$_2$CO$_3$ (3 eq) CD$_3$I (2.2 eq) Acetone (8 vol) 28-35° C., 36 hours | 198.9 g | 83.7% | 93.1% |
| 2 | 25 g | K$_2$CO$_3$ (3 eq) CH$_3$I (2.2 eq) Acetone (8 vol) 38-40° C., 36 hours | 21 g | 72.9% | 95.8% |

TABLE 6

Optimization of reaction conditions by varying phase transfer catalyst and methyl iodide equivalents

| Exp. No. | Batch Size | Phase Transfer Catalyst (eq) | CH$_3$I (eq) | Base (eq) | Solvent/ Conditions | Result |
|---|---|---|---|---|---|---|
| 1 | 10 g | Tetrabutyl ammonium bromide (0.05) | 3 | K$_2$CO$_3$ (3.0) | Acetone 35-45° C., 45 hours | Worked well |
| 2 | 10 g | Tetrabutyl ammonium bromide (0.08) | 3 | K$_2$CO$_3$ (3.0) | Acetone 35-45° C., 45 hours | Worked well |
| 3 | 10 g | None | 2.2 | Cs$_2$CO$_3$ (2.0) | Acetone 35-45° C., 20 hours | 1.5% Formanide methylation, 5% mono-methylated phenol remaining |
| 4 | 10 g | None | 2.5 | Cs$_2$CO$_3$ (2.0) | Acetone 35-45° C., 20 hours | 2% Formanide methylation, 3% mono-methylated phenol remaining |
| 5 | 10 g | Tetrabutyl ammonium bromide (0.05) | 2.2 | K$_2$CO$_3$ (3.0) | Acetone 35-45° C., 20 hours | Worked well |
| 6 | 10 g | Tetrabutyl ammonium bromide (0.05) | 2.5 | K$_2$CO$_3$ (3.0) | Acetone 35-45° C., 20 hours | Worked well |

TABLE 7

Optimization of reaction conditions by varying phase transfer catalyst

| Exp. No. | Batch Size | Reaction Conditions | Product Quantity | Product Yield | HPLC Purity |
|---|---|---|---|---|---|
| 1 | 30 g | K$_2$CO$_3$ (3 eq) CH$_3$I (2.2 eq) Acetone (8 vol) Tetrabutylammonium bromide (0.05) 38-42° C., 36 hours | 28 g | 82.3% | — |
| 2 | 25 g | K$_2$CO$_3$ (3 eq) CH$_3$I (2.2 eq) Acetone (8 vol) 18-Crown-6 (0.1) 38-42° C., 36 hours | 24 g | 81% | — |
| 3 | 25 g | K$_2$CO$_3$ (3 eq) CH$_3$I (2.2 eq) Acetone (8 vol) Tetrabutylammonium iodide (0.05) 38-42° C., 36 hours | 23 g | 79.8% | 83.4% |

TABLE 8

Optimization of reaction conditions by varying phase transfer catalyst quantity

| Exp. No. | Batch Size | Reaction Conditions | Product Quantity | Product Yield | HPLC Purity |
|---|---|---|---|---|---|
| 1 | 50 g | $K_2CO_3$ (3 eq) $CH_3I$ (2.2 eq) Acetone (8 vol) Tetrabutylammonium bromide (0.05) 38-42° C., 36 hours | 50 g | 86.6% | 93.9% |
| 2 | 25 g | $K_2CO_3$ (3 eq) $CH_3I$ (2.2 eq) Acetone (8 vol) Tetrabutylammonium bromide (0.01) 38-42° C., 36 hours | 22 g | 76.3% | 90.78% |
| 3 | 25 g | $K_2CO_3$ (3 eq) $CH_3I$ (2.2 eq) Acetone (8 vol) Without tetrabutylammonium bromide 38-42° C., 36 hours | 21 g | 72.9% | 95.85% |

Representative Example—Step 1

$d_6$-N-(2-(3,4-dimethoxy-phenyl)-ethyl)-formamide

N-(2-(3,4-dihydroxy-phenyl)-ethyl)-formamide (190 g, 1.049 mol, 1.00 eq) was charged with acetone (1.52 L, 8.0 vol), followed by $K_2CO_3$ (434 g, 3.149 mol, 3.00 eq) at 25-30° C. $CD_3I$ (334 g, 2.309 mol, 2.20 eq) was added to the reaction mixture over 1 hour at 25-30° C. The reaction temperature was maintained for 36 hours at 25-35° C. The reaction was filtered, the filtrate was distilled under reduced pressure, and the crude product was partitioned between dichloromethane (1.14 L, 6.0 vol) and water (760 mL, 4.0 vol). The layers were separated and the organic layer was washed twice with 3% aqueous NaOH solution (2×760 mL, 2×4.0 vol) followed by water (760 mL, 4.0 vol). The organic layer was distilled under reduced pressure to give 158 g crude $d_6$-N-(2-(3,4-dimethoxy-phenyl)-ethyl)-formamide.

Step 2

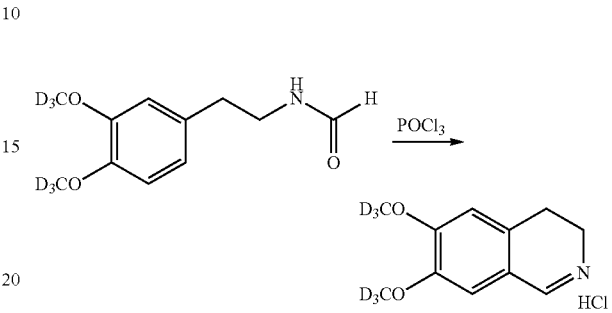

Optimization of Reaction Conditions
General Procedure:

N-(2-(3,4-dimethoxy-phenyl)-ethyl)-formamide is charged with solvent and $POCl_3$ at 10-15° C. The mixture is heated to an elevated temperature for 1 or 2 hours and then is cooled to ambient temperature, after which a quenching solvent (for example, a protic solvent such as an alcohol) is added and the mixture is stirred for 1 hour followed by addition of an anti-solvent if applicable. In some cases, $d_6$-6,7-dimethoxy-3,4-dihydroisoquinoline hydrochloride precipitates in the form of a salt directly from the reaction mixture. In others, $d_6$-6,7-dimethoxy-3,4-dihydroisoquinoline is isolated after acid-base workup.

TABLE 9

Optimization of reaction conditions by varying the solvent

| Exp. No. | Batch Size | Reaction Conditions | Quenching/ Anti-Solvent | Product Quantity | Product Yield | HPLC Purity |
|---|---|---|---|---|---|---|
| 1 | 93 g | $POCl_3$ (1 eq) Acetonitrile (10 vol) 80-85° C., 2 hours | None | 49 g | 57.6% | 90.0% |
| 2 | 200 g | $POCl_3$ (1 eq) Toluene (2 vol) 90-95° C., 1 hours | None | 112 g | 61.5% | 84.6% |
| 3 | 20 g | $POCl_3$ (1 eq) MTBE* (4 vol) 0-30° C. | None | sticky mass | — | — |
| 4 | 20 g | $POCl_3$ (1 eq) DCM* (2 vol) 0-30° C. | None | sticky mass | — | — |

*DCM = Dichloromethane; MTBE = Methyl tert-butyl ether.

TABLE 10

Optimization of reaction conditions by varying quenching solvent and anti-solvent (reaction solvent toluene)

| Exp. No. | Batch Size | Reaction Conditions | Quenching/ Anti-Solvent | Product Quantity | Yield | HPLC Purity |
|---|---|---|---|---|---|---|
| 1 | 48 g | $POCl_3$ (1.8 eq) Toluene (2 vol) 90-95° C., 1 hour | Ethanol (3.8 eq) MTBE* (4 vol) | Product not obtained as a free solid | — | — |

TABLE 10-continued

Optimization of reaction conditions by varying quenching solvent and anti-solvent (reaction solvent toluene)

| Exp. No. | Batch Size | Reaction Conditions | Quenching/ Anti-Solvent | Product Quantity | Yield | HPLC Purity |
|---|---|---|---|---|---|---|
| 2 | 48 g | $POCl_3$ (distilled, 1.8 eq) Toluene (2 vol) 90-95° C., 1 hour | Ethanol (3.8 eq) MTBE* (4 vol) | 20.2 g | 46% | 91.9% |
| 3 | 50 g | $POCl_3$ (1 eq) Toluene (2 vol) 90-95° C., 1 hour | Ethyl Acetate (2 vol) Ethyl Acetate/ HCl (2 vol) | 35 g | 76% | — |
| 4 | 20 g | $POCl_3$ (distilled, 1.8 eq) Toluene (2 vol) 40-45° C., 1 hour | Ethanol (2.4 eq) MTBE* (4 vol) | Product not obtained as a free solid | — | — |
| 5 | 50 g | $POCl_3$ (distilled, 1.8 eq) Toluene (2 vol) | Ethanol (3.8 eq) MTBE* (4 vol) 80-85° C., 1 hour, seeded with product | Product not obtained as a free solid | — | — |
| 6 | 28 g | $POCl_3$ (1.8 eq) Toluene (2 vol) 90-95° C., 2 hours | Ethanol (3.8 eq) MTBE* (4 vol) | 24 g | >100% | Isolated by acid-base workup |
| 7 | 25 g | $POCl_3$ (1.8 eq) Toluene (2 vol) 90-95° C., 2 hours | IPA* (3.8 eq) MTBE* (4 vol) 12 hours | 14.5 g | 53.2% | 80.2% (black solid) |
| 8 | 25 g | $POCl_3$ (1.8 eq) Toluene (2 vol) 90-95° C., 2 hours | 1-Butanol (3.8 eq) MTBE* (4 vol) 12 hours | 20.1 g | 73.5% | 80.1% (black solid) |
| 9 | 25 g | $POCl_3$ (1.8 eq) Toluene (2 vol) 90-95° C., 2 hours | 1-Propanol (3.8 eq) Cyclohexane (4 vol) 12 hours | Product not obtained as a free solid | — | — |

*IPA = Isopropyl alcohol; MTBE = Methyl tert-butyl ether.

TABLE 11

Optimization of reaction conditions by varying quenching solvent and anti-solvent (reaction solvent acetonitrile)

| Exp. No. | Batch Size | Reaction Conditions | Quenching/ Anti-Solvent | Product Quantity | Yield | HPLC Purity |
|---|---|---|---|---|---|---|
| 1 | 100 g | $POCl_3$ (1.8 eq) Acetonitrile (2 vol) 80-85° C., 1 hour | Ethanol (3.8 eq) MTBE* (4 vol) 12 hours, seeded with product | 110 g | — | 93.3% (hygroscopic) |
| 2 | 25 g | $POCl_3$ (1.8 eq) Acetonitrile (2 vol) 80-85° C., 2 hours | IPA* (3.8 eq) MTBE* (4 vol) 12 hours, | 17 g | 62.4% | 87.1% (black solid) |
| 3 | 25 g | $POCl_3$ (1.8 eq) Acetonitrile (2 vol) 80-85° C., 2 hours | 1-Butanol (3.8 eq) MTBE* (4 vol) 12 hours | 17.3 g | 63.8% | 95.6% (grey solid) |
| 5 | 25 g | $POCl_3$ (1.8 eq) Acetonitrile (2 vol) 80-85° C., 2 hours | t-Butanol (3.8 eq) MTBE* (4 vol) 12 hours | Solid not isolated | — | — |
| 6 | 25 g | $POCl_3$ (1.8 eq) Acetonitrile (2 vol) 80-85° C., 2 hours | 1-Propanol (3.8 eq) MTBE* (4 vol) 12 hours | 17 g | 62.4% | 88.8% (gray solid) |
| 7 | 25 g | $POCl_3$ (1.8 eq) Acetonitrile (2 vol) 80-85° C., 2 hours | 1-Pentanol (3.8 eq) MTBE* (4 vol) 12 hours | 13.4 g | 49.2% | Brown solid |

TABLE 11-continued

Optimization of reaction conditions by varying quenching solvent and anti-solvent (reaction solvent acetonitrile)

| Exp. No. | Batch Size | Reaction Conditions | Quenching/ Anti-Solvent | Product Quantity | Yield | HPLC Purity |
|---|---|---|---|---|---|---|
| 8 | 25 g | POCl$_3$ (1.8 eq) Acetonitrile (2 vol) 80-85° C., 2 hours | 2-methyl propanol (3.8 eq) MTBE* (4 vol) 12 hours | 12.77 g | 46.9% | 87.6% (gray solid) |

*IPA = Isopropyl alcohol; MTBE = Methyl tert-butyl ether.

TABLE 12

Optimization of reaction conditions by varying anti-solvent (reaction solvent acetonitrile, 1-butanol as a quenching solvent)

| Exp. No. | Batch Size | Reaction Conditions | Quenching/ Anti-Solvent | Product Quantity | Product Yield | HPLC Purity |
|---|---|---|---|---|---|---|
| 1 | 25 g | POCl$_3$ (1.8 eq) Acetonitrile (2 vol) 80-85° C., 2 hours | 1-butanol (3.8 eq) Ethyl acetate (4 vol) 12 hours | 13.3 g | 48.8% | 91.9% |
| 2 | 25 g | POCl$_3$ (1.8 eq) Acetonitrile (2 vol) 80-85° C., 2 hours | 1-butanol (3.8 eq) Isopropyl acetate (4 vol) 12 hours | 14.83 g | 54.5% | 94.4% |
| 3 | 25 g | POCl$_3$ (1.8 eq) Acetonitrile (2 vol) 80-85° C., 2 hours | 1-butanol (3.8 eq) 2-methyl-THF* (4 vol) 12 hours | 14.2 g | 52.2% | 93.3% |
| 4 | 25 g | POCl$_3$ (1.8 eq) Acetonitrile (2 vol) 80-85° C., 2 hours | 1-butanol (3.8 eq) Ethyl acetate/ HCl (4 vol) 12 hours | 13.0 g | 47.7% | 94.2% |
| 5 | 25 g | POCl$_3$ (1.8 eq) Acetonitrile (2 vol) 80-85° C., 2 hours | 1-butanol (3.8 eq) MTBE* (4 vol) 12 hours | 18.3 g | 67.2% | 93.5% |
| 6 | 25 g | POCl$_3$ (1.8 eq) Acetonitrile (2 vol) 80-85° C., 2 hours | 1-butanol (3.8 eq) MTBE* (8 vol) 12 hours | 17.5 g | 64.3% | 91.3% |

*MTBE = Methyl tert-butyl ether; 2-methyl-THF = 2-methyltetrahydrofuran (4 vol).

TABLE 13

Optimization of reaction conditions by varying equivalents of 1-butanol (reaction solvent acetonitrile, 1-butanol as a quenching solvent)

| Exp. No. | Batch Size | Reaction Conditions | Quenching/ Anti-Solvent | Product Quantity | Product Yield | HPLC Purity |
|---|---|---|---|---|---|---|
| 1 | 25 g | POCl$_3$ (1.8 eq) Acetonitrile (2 vol) 80-85° C., 2 hours | 1-butanol (6.0 eq) MTBE* (4 vol) 12 hours | 14.7 g | 54% | 84.1% |
| 2 | 28 g | POCl$_3$ (1.8 eq) Acetonitrile (2 vol) 80-85° C., 2 hours | 1-butanol (3.8 eq) MTBE* (4 vol) 12 hours | 21.3 g | 70% | 94.6% |

*MTBE = Methyl tert-butyl ether;

TABLE 14

Optimization of reaction conditions by using methyl tert-butyl ether as reaction solvent and varying the quenching solvent

| Exp. No. | Batch Size | Reaction Conditions | Quenching/ Anti-Solvent | Product Quantity | Product Yield | HPLC Purity |
|---|---|---|---|---|---|---|
| 1 | 25 g | POCl₃ (1.8 eq) MTBE* (4 vol) 55-60° C., 2 hours | Ethanol (3.8 eq) 12 hours | Solid not isolated | — | — |
| 2 | 25 g | POCl₃ (1.8 eq) MTBE* (4 vol) 45-50° C., 2 hours | 1-butanol (3.8 eq) 12 hours | 10.5 g | 38.5% | 74.4% (brown solid) |

*MTBE = Methyl tert-butyl ether;

TABLE 15

Optimization of reaction conditions by varying the equivalents of POCl₃ used

| Exp. No. | Batch Size | Reaction Conditions | Quenching/ Anti-Solvent | Product Quantity | Product Yield | HPLC Purity |
|---|---|---|---|---|---|---|
| 1 | 50 g | POCl₃ (0.5 eq) Acetonitrile (2 vol) 80-85° C., 2 hours | 1-butanol (3.8 eq) MTBE* (4 vol) 12 hours | — | — | Product obtained as a gummy solid |
| 2 | 50 g | POCl₃ (1.0 eq) Acetonitrile (2 vol) 80-85° C., 2 hours | 1-butanol (3.8 eq) MTBE* (4 vol) 12 hours | — | — | Product obtained as a gummy solid |
| 3 | 25 g | POCl₃ (1.8 eq) Acetonitrile (2 vol) 80-85° C., 2 hours | 1-butanol (3.8 eq) MTBE* (4 vol) 12 hours | 17.3 g | 63.8% | 98.6% |

Representative Example—Step 2 d₆-6,7-Dimethoxy-3,4-dihydroisoquinoline hydrochloride

To the crude d₆-N-(2-(3,4-dimethoxy-phenyl)-ethyl)-formamide from step 1, (158 g, 0.734 mol, 1.00 eq), acetonitrile (316 mL, 2.0 vol) was added followed by POCl₃ (202 g, 1.322 mol, 1.80 eq) at 10-15° C. The reaction mixture was heated to reflux for 2 hours and then cooled to 25-35° C. The temperature was maintained for 12 hours after which it was quenched with n-butanol (255 mL, 2.79 mol, 3.8 eq) and methyl tert-butyl ether (1.26 L, 8.0 vol). The precipitated product was filtered, washed with ethyl acetate (632 mL, 4.0 vol), and dried under vacuum. The crude product was further purified by slurrying in 10% Ethanol in MTBE (944 mL, 8.0 vol) whereupon an orange brown product (108 g, yield=44.0%) was obtained after drying. $^1$H NMR (300 MHz, CDCl₃), δ 14.456 (br s, 1H), 9.105-9.133 (d, 1H, J=8.4), 7.497 (s, 1H), 6.806 (s, 1H), 3.951-4.000 (t, 2H, J=7.5), 3.089-3.144 (t, 2H, J=8.4); LC-MS: m/z=198.06 (MH)⁺.

Step 3—Optional purification of d₆-6,7-dimethoxy-3,4-dihydroisoquinoline hydrochloride To increase the purity of d₆-6,7-dimethoxy-3,4-dihydroisoquinoline hydrochloride various purification procedures were attempted.

TABLE 16

Recrystallization of d₆-6,7-dimethoxy-3,4-dihydroisoquinoline hydrochloride

| Exp. No. | Batch Size | Reaction Conditions | Product Quantity | Product Yield | HPLC Purity |
|---|---|---|---|---|---|
| 1 | 5 g | 6,7-Dimethoxy-3,4-dihydroisoquinoline hydrochloride (1 eq) Ethanol (3 vol) 60-65° C., 1 hour Cooled and filtered at 25-30° C. | 2.1 g | 42% | 94.5% |
| 2 | 5 g | 6,7-Dimethoxy-3,4-dihydroisoquinoline hydrochloride (1 eq) Ethanol (8 vol) 75-80° C., 16 hours Cooled and filtered at 25-30° C. | 1.4 g | 28.0% | 89.0% |
| 3 | 5 g | 6,7-Dimethoxy-3,4-dihydroisoquinoline hydrochloride (1 eq) 1-Propanol (8 vol) 95-100° C., 16 hours Cooled and filtered at 25-30° C. | 1.02 g | 20.4% | 84.8% |
| 4 | 5 g | 6,7-Dimethoxy-3,4-dihydroisoquinoline hydrochloride (1 eq) 1-Butanol (8 vol) 115-120° C., 16 hours Cooled and filtered at 25-30° C. | 0.85 g | 17.0% | 76.0% |

TABLE 16-continued

Recrystallization of d<sub>6</sub>-6,7-dimethoxy-3,4-dihydroisoquinoline hydrochloride

| Exp. No. | Batch Size | Reaction Conditions | Product Quantity | Product Yield | HPLC Purity |
|---|---|---|---|---|---|
| 5 | 5 g | 6,7-Dimethoxy-3,4-dihydroisoquinoline hydrochloride (1 eq) 1-Pentanol (8 vol) 135-140° C., 16 hours Cooled and filtered at 25-30° C. | 1.19 g | 23.8% | 85.7% |

TABLE 17

Reslurry and washing of d$_6$-6,7-dimethoxy-3,4-dihydroisoquinoline hydrochloride

| Exp. No. | Batch Size | Reaction Conditions | Product Quantity | Product Yield | HPLC Purity |
|---|---|---|---|---|---|
| 1 | 2 g | 6,7-Dimethoxy-3,4-dihydroisoquinoline hydrochloride (1 eq) Acetone (3 vol) Stirred at 25-30° C. for 2 hours, then filtered and dried | 1.75 g | 83.3% | 93.3% |
| 2 | 2 g | 6,7-Dimethoxy-3,4-dihydroisoquinoline hydrochloride (1 eq) Acetonitrile (2 vol) Stirred at 25-30° C. for 2 hours, then filtered and dried | 1.21 g | 60% | 94.5% |
| 3 | 2 g | 6,7-Dimethoxy-3,4-dihydroisoquinoline hydrochloride (1 eq) Ethanol/acetonitrile/acetone (1:1:8) (3 vol) Stirred at 25-30° C. for 2 hours, then filtered and dried | 1.35 g | 67.5% | — |
| 4 | 2 g | 6,7-Dimethoxy-3,4-dihydroisoquinoline hydrochloride (1 eq) Methanol/ethyl acetate (5:95) (3 vol) Stirred at 25-30° C. for 2 hours, then filtered and dried | 1.78 g | 89% | — |
| 5 | 2 g | 6,7-Dimethoxy-3,4-dihydroisoquinoline hydrochloride (1 eq) Methanol/ethyl acetate (5:95) (3 vol) Stirred at 25-30° C. for 1 hour, then filtered and dried | 1.34 g | 67% | — |
| 6 | 2 g | 6,7-Dimethoxy-3,4-dihydroisoquinoline hydrochloride (1 eq) Ethanol/acetone/ethyl acetate (1:1:8) (3 vol) Stirred at 25-30° C. for 1 hour, then filtered and dried | 1.46 g | 73% | — |
| 7 | 1 g | 6,7-Dimethoxy-3,4-dihydroisoquinoline hydrochloride (1 eq) Ethanol/ethyl acetate (1:9) (3 vol) Stirred at 25-30° C. for 1 hour, then filtered and dried | 0.55 g | 55% | — |
| 8 | 5 g | 6,7-Dimethoxy-3,4-dihydroisoquinoline hydrochloride (1 eq) Ethyl acetate (5 vol) Stirred at 28-32° C. for 16 hours, then filtered and dried | 4.8 g | 96.0% | 93.5% |
| 9 | 5 g | 6,7-Dimethoxy-3,4-dihydroisoquinoline hydrochloride (1 eq) Methyl tert-butyl ether (5 vol) Stirred at 28-32° C. for 16 hours, then filtered and dried | 4.87 g | 97.4% | 79.1% |
| 10 | 5 g | 6,7-Dimethoxy-3,4-dihydroisoquinoline hydrochloride (1 eq) Acetone (3 vol) Stirred at 28-32° C. for 16 hours, then filtered and dried | 4.31 g | 86.2% | 94.1% |
| 11 | 5 g | 6,7-Dimethoxy-3,4-dihydroisoquinoline hydrochloride (1 eq) Acetonitrile (3 vol) Stirred at 28-32° C. for 16 hours, then filtered and dried | 1.63 g | 32.6% | 90.9% |
| 12 | 5 g | 6,7-Dimethoxy-3,4-dihydroisoquinoline hydrochloride (1 eq) Methyl tert-butyl ether (6 vol) 50-55° C. 1-butanol (12 vol) Stirred at 28-32° C. for 16 hours, then filtered and dried | 3.4 g | 68% | 91.7% |
| 13 | 5 g | 6,7-Dimethoxy-3,4-dihydroisoquinoline hydrochloride (1 eq) Methyl tert-butyl ether/ethanol (9:1) (6 vol) Stirred at 28-32° C. for 16 hours, then filtered and dried | 4.3 g | 86% | 87.6% |
| 14 | 150 g | 6,7-Dimethoxy-3,4-dihydroisoquinoline hydrochloride (1 eq) Methyl tert-butyl ether/ethanol (9:1) (6 vol) Stirred at 28-32° C. for 16 hours, then filtered and dried | 138 g | 92% | 99.0% |

EXAMPLE 3

(RR,SS)-1,3,4,6,7-11b-Hexahydro-9,10-di(methoxy-$d_3$)-3-(2-methylpropyl)-2H-benzo[a]quinolizin-2-one ((+/−)-$d_6$-Tetrabenazine)

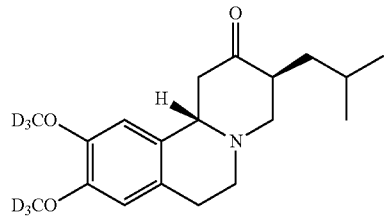

Step 1

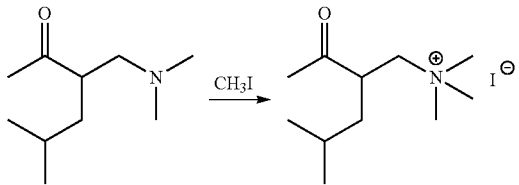

Representative Example—Step 1

2-acetyl-N,N,N,4-tetramethyl-1-pentanaminium iodide

3-[(dimethylamino)methyl]-5-methyl-hexan-2-one (90 g, 0.526 mol, 1.00 eq) was charged with methyl tert-butyl ether (1.35 L, 15.0 vol) and cooled 0-10° C. Methyl iodide (171 g, 1.209 mol, 2.3 eq) was added slowly to the reaction mixture and stirred for 15 hours at 25-35° C. The reaction was warmed to 35-40° C. for 2 hours. The precipitated solid was filtered under nitrogen and was washed with methyl tert-butyl ether (900 mL, 10.0 vol). The crude product was further purified by slurrying in ethyl acetate (1.46 L, 10 vol) and filtered to give 2-acetyl-N,N,N,4-tetramethyl-1-pentanaminium iodide (146 g) as a white solid.

Step 2

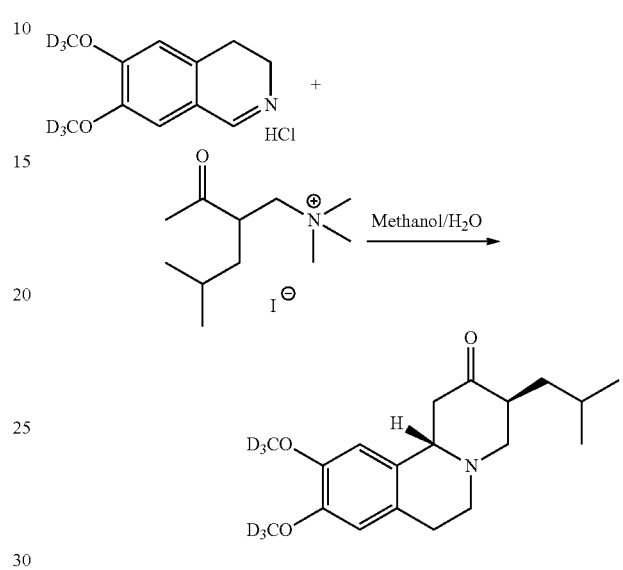

Optimization of Reaction Conditions

General Procedure:

2-acetyl-N,N,N,4-tetramethyl-1-pentanaminium iodide is charged to a suspension containing $d_6$-6,7-dimethoxy-3,4-dihydroisoquinoline (hydrochloride or freebase, 1.00 eq) and solvent. If $d_6$-6,7-dimethoxy-3,4-dihydroisoquinoline hydrochloride is used, a base is added to the reaction mixture at room temperature. The reaction mixture is stirred at the appropriate temperature, cooled, and water is added. The reaction mass is filtered and the solids are washed with water and dried to afford the title compound [The (RR, SS)-diastereomer of $d_6$-tetrabenazine is the desired product].

TABLE 18

Optimization of the reaction by varying the solvent

| Exp. No. | Batch Size | Reaction Conditions | Product Quantity | Product Yield | HPLC Purity |
|---|---|---|---|---|---|
| 1 | 30 g | 6,7-Dimethoxy-3,4-dihydro isoquinoline free base (1 eq) 2-acetyl-N,N,N,4-tetramethyl-1-pentanaminium iodide (0.75 eq) Water (6 vol) 100° C., 48 hour | 20.3 g | 40.7% | 98.8% 0.56% Diastereomer impurity* |
| 2 | 10 g | 6,7-Dimethoxy-3,4-dihydro isoquinoline free base (1 eq) 2-acetyl-N,N,N,4-tetramethyl-1-pentanaminium iodide (0.75 eq) Methanol (6 vol) 65-70° C., 48 hour | 1.4 g | 8.3% | 97.8% 1.45% Diastereomer impurity* |
| 3 | 10 g | 6,7-Dimethoxy-3,4-dihydro isoquinoline free base (1 eq) 2-acetyl-N,N,N,4-tetramethyl-1-pentanaminium iodide (0.75 eq) Ethanol (6 vol) 75-80° C., 48 hour | 1.4 g | 8.3% | 98.1% 0.75% Diastereomer impurity* |

TABLE 18-continued

Optimization of the reaction by varying the solvent

| Exp. No. | Batch Size | Reaction Conditions | Product Quantity | Product Yield | HPLC Purity |
|---|---|---|---|---|---|
| 4 | 10 g | 6,7-Dimethoxy-3,4-dihydro isoquinoline free base (1 eq) 2-acetyl-N,N,N,4-tetramethyl-1-pentanaminium iodide (0.75 eq) Methanol/water (1:1) (6 vol) 45-50° C., 90 hour | 6.8 g | 40.8% | 99.1% 0.04% Diastereomer impurity* |

*The diastereomer impurity is the (RS, SR) diastereomer of $d_6$-tetrabenazine.

Tables 19 and 20—In-process HPLC results

| | Ex. 2 Methanol | | | Ex. 3 - Ethanol | | |
|---|---|---|---|---|---|---|
| Time | SM* | Product | Diaste-reomer* | SM* | Product | Diaste-reomer* |
| 6 h | 17.2% | 12.5% | 2.6% | 3.3% | 12.4% | 3.0% |
| 18 h | 4.3% | 17.1% | 3.8% | 0.2% | 14.6% | 3.9% |
| 24 h | 1.2% | 16.8% | 4.5% | 0.1% | 17.2% | 5.2% |
| 30 h | 0.5% | 14.0% | 3.2% | 0.3% | 12.4% | 3.3% |
| 42 h | 0.3% | 12.3% | 3.1% | 0.2% | 9.6% | 2.6% |
| 48 h | 0.3% | 12.1% | 2.9% | 0.2% | 12.0% | 2.9% |
| Product | — | 97.8% | 1.4% | — | 98.1% | 0.75% |
| Wt (g) | | 1.38 | | | 1.38 | |
| Y (%) | | 8.3 | | | 8.3 | |

*SM = Starting material - [6,7-Dimethoxy-3,4-dihydro isoquinoline]; The diastereomer impurity is the (RS,SR) diastereomer of $d_6$-tetrabenazine.

| | Ex. 4 - Methanol:Water (1:1) | | |
|---|---|---|---|
| Time | SM* | Product | Diastereomer* |
| 6 h | — | — | — |
| 18 h | 3.1% | 21.% | 0.7% |
| 24 h | — | — | — |
| 30 h | — | — | — |
| 42 h | 1.8% | 23.9% | 0.5% |
| 48 h | — | — | — |
| 90 h | — | 28.1% | 1.0% |
| Product | — | 99.1% | 0.04% |
| Wt (g) | | 6.78 g | |
| Y (%) | | 40.8 | |

*SM = Starting material - [6,7-Dimethoxy-3,4-dihydro isoquinoline];
The diastereomer impurity is the (RS, SR) diastereomer of $d_6$-tetrabenazine.

TABLE 21

Optimization of the reaction by varying the reaction temperature

| Exp. No. | Batch Size | Reaction Conditions | Product Quantity | Product Yield | HPLC Purity |
|---|---|---|---|---|---|
| 1 | 8 g | 6,7-Dimethoxy-3,4-dihydroiso-quinoline hydrochloride (1 eq) 2-acetyl-N,N,N,4-tetramethyl-1-pentanaminium iodide (1.08 eq) Methanol/water (1:1) (6 vol) $K_2CO_3$ (1 eq) 45-50° C., 63 hour | 8.3 g | 74.5% | 99.1% 0.04% Diastereomer impurity* |
| 2 | 8 g | 6,7-Dimethoxy-3,4-dihydroiso-quinoline hydrochloride (1 eq) 2-acetyl-N,N,N,4-tetramethyl-1-pentanaminium iodide (1.08 eq) Methanol/water (1:1) (6 vol) $K_2CO_3$ (1 eq) 25-30° C., 63 hour | 8.5 g | 76.7% | 99.1% 0.04% Diastereomer impurity* |
| 3 | 8 g | 6,7-Dimethoxy-3,4-dihydroiso-quinoline hydrochloride (1 eq) 2-acetyl-N,N,N,4-tetramethyl-1-pentanaminium iodide (1.08 eq) Methanol/water (1:1) (6 vol) $K_2CO_3$ (1 eq) 65-70° C., 63 hour | 8.3 g | 75% | 99.1% 0.1% Diastereomer impurity* |

*The diastereomer impurity is the (RS, SR) diastereomer of $d_6$-tetrabenazine.

Tables 22 and 23—In-process HPLC results

| | Ex. 3 - Methanol:Water (1:1) 65-70° C. | | | Ex. 2 - Methanol:Water (1:1) 45-50° C. | | |
|---|---|---|---|---|---|---|
| Hours | SM* | Product | Diastereomer* | SM* | Product | Diastereomer* |
| 15 h | 0.8% | 8.1% | 0.5% | — | 23.5% | 0.1% |
| 23 h | — | 33.1% | 0.5% | — | 17.1% | 0.2% |
| 39 h | — | 14.3% | 0.4% | — | 22.0% | 0.1% |
| 47 h | — | 17.9% | 0.5% | — | 35.9% | 0.3% |
| 63 h | — | 44.4% | 0.8% | — | 58.2% | 0.4% |
| Crude | — | 88.6% | 1.8% | — | 92.3% | 0.6% |
| After EA | — | 91.6% | 1.3% | — | 95.2% | 0.6% |
| Final Product | — | 99.19% | 0.1% | — | 99.15% | 0.04% |
| | Wt (g) | 8.38 | | Wt (g) | 8.32 | |
| | Y (%) | 75 | | Y (%) | 74.5 | |

*SM = Starting material - [6,7-Dimethoxy-3,4-dihydro isoquinoline]; The diastereomer impurity is the (RS,SR) diastereomer of $d_6$-tetrabenazine.

| | Ex. 1 - Methanol:Water (1:1) 25-30° C. | | |
|---|---|---|---|
| Hours | SM* | Product | Diastereomer* |
| 15 h | — | 31.6% | 0.2% |
| 23 h | — | 29.5% | 0.2% |
| 39 h | — | 35.2% | 0.2% |
| 47 h | — | 20.9% | 0.1% |
| 63 h | — | 63.4% | 0.3% |
| Crude | — | 95.7% | 0.5% |
| After EA* treatment | — | 95.5% | 0.4% |
| Final Product | — | 99.16% | 0.04% |
| | Wt (g) | 8.56 | |
| | Y (%) | 76.7 | |

*SM = Starting material - [6,7-Dimethoxy-3,4-dihydro isoquinoline];
EA = Ethyl Acetate;
The diastereomer impurity is the (RS, SR) diastereomer of $d_6$-tetrabenazine.

TABLE 24

Optimization of the reaction by varying the solvent mixture ratio

| Exp. No. | Batch Size | Reaction Conditions | Product Quantity | Product Yield | HPLC Purity |
|---|---|---|---|---|---|
| 1 | 8 g | 6,7-Dimethoxy-3,4-dihydroisoquinoline hydrochloride (1 eq) 2-acetyl-N,N,N,4-tetramethyl-1-pentanaminium iodide (1.08 eq) Methanol/water (1:3) (6 vol) $K_2CO_3$ (1 eq) 45-50° C., 63 hour | 8.5 g | 76.9% | 98.9% 0.09% undesired isomer |
| 2 | 8 g | 6,7-Dimethoxy-3,4-dihydroisoquinoline hydrochloride (1 eq) 2-acetyl-N,N,N,4-tetramethyl-1-pentanaminium iodide (1.08 eq) Methanol/water (3:1) (6 vol) $K_2CO_3$ (1 eq) 45-50° C., 63 hour | 8.6 g | 77.1% | 99.6% 0.03% undesired isomer |
| 3 | 10 g | 6,7-Dimethoxy-3,4-dihydroisoquinoline hydrochloride (1 eq) 2-acetyl-N,N,N,4-tetramethyl-1-pentanaminium iodide (1.08 eq) Methanol/water (4:1) (6 vol) $K_2CO_3$ (1 eq) 45-50° C., 63 hour | 9.6 g | 68.9% | 99.3% off-white product |
| 4 | 10 g | 6,7-Dimethoxy-3,4-dihydroisoquinoline hydrochloride (1 eq) 2-acetyl-N,N,N,4-tetramethyl-1-pentanaminium iodide (1.08 eq) Methanol (6 vol) $K_2CO_3$ (1 eq) 45-50° C., 63 hour | 7.6 g | 54.4% | 99.2% |

Tables 25 and 26—In-process HPLC results

| | Ex. 1 - Methanol:Water (1:3) 45-50° C. | | | Ex. 2 - Methanol:Water (3:1) 45-50° C. | | |
|---|---|---|---|---|---|---|
| Hours | SM* | Product | Diastereomer* | SM* | Product | Diastereomer* |
| 24 h | — | 44.7% | 0.4% | — | 18.6% | 0.5% |
| 48 h | — | 54.8% | 0.6% | — | 18.9% | 0.5% |
| 63 h | — | 70.0% | 0.8% | — | 16.0% | 0.8% |
| Crude | — | 91.1% | 1.3% | — | 98.5% | 0.4% |
| After EA* treatment | — | 92.6% | 1.0% | — | 98.7% | 0.4% |
| Final Product | — | 98.98% | 0.09% | — | 99.64% | 0.03% |
| Wt (g) | | 8.59 | | | 8.61 | |
| Y (%) | | 76.9 | | | 77.1 | |

*SM = Starting material - [6,7-Dimethoxy-3,4-dihydro isoquinoline]; EA = Ethyl Acetate;
The diastereomer impurity is the (RS,SR) diastereomer of $d_6$-tetrabenazine.

| | Ex. 3 - Methanol:Water (4:1) 45-50° C. | | | Ex. 4 - Methanol, 45-50° C. | | |
|---|---|---|---|---|---|---|
| Hours | SM* | Product | Diastereomer* | SM* | Product | Diastereomer* |
| 24 h | — | — | — | — | — | — |
| 48 h | — | — | — | — | — | — |
| 63 h | — | 17.75% | 2.57% | — | 17.75% | 2.57% |
| Crude | — | 97.97% | 0.59% | — | 97.97% | 0.59% |
| After EA* treatment | — | 98.15% | 0.35% | — | 98.15% | 0.35% |
| Final Product | — | 99.28% | 0.03% | — | 99.28% | 0.03% |
| | | 7.58 | | | 7.58 | |
| | | 54.4 | | | 54.4 | |

*SM = Starting material - [6,7-Dimethoxy-3,4-dihydro isoquinoline]; EA = Ethyl Acetate;
The diastereomer impurity is the (RS,SR) diastereomer of $d_6$-tetrabenazine.

Tables 28 and 29—In-process HPLC results

| | Ex. 1 - Methanol:Water (3:1) 45-50° C., 24 h | | | Ex. 2 - Methanol:Water (3:1) 45° C., 48 h | | |
|---|---|---|---|---|---|---|
| Hours | SM* | Product | Diastereomer* | SM* | Product | Diastereomer* |
| 24 h | 1.52% | 15.65% | 1.38% | — | — | — |
| 48 h | — | — | — | — | 23.73% | 0.66% |
| 63 h | — | — | — | — | — | — |
| Crude | — | 92.1% | 1.96% | — | 91.83% | 1.53% |
| After EA* treatment | — | 91.96% | 1.17% | — | 91.64% | 1.57% |
| Final Product | — | 99.25% | 0.08% | — | 99.58% | 0.03% |
| Wt (g) | | 8.5 | | | 9.4 | |
| Y (%) | | 61 | | | 67.4 | |

*SM = Starting material - [6,7-Dimethoxy-3,4-dihydro isoquinoline]; EA = Ethyl Acetate;
The diastereomer impurity is the (RS,SR) diastereomer of $d_6$-tetrabenazine.

| | Ex. 3 - Methanol:Water (3:1) 45° C., 63 h | | |
|---|---|---|---|
| Hours | SM* | Product | Diastereomer* |
| 24 h | — | — | — |
| 48 h | — | — | — |
| 63 h | — | 13.63% | 0.71% |
| Crude | — | 98.43% | 0.34% |
| After EA* treatment | — | 98.24% | 0.45% |
| Final Product | — | 99.29% | 0.04% |
| Wt (g) | | 9.2 | |
| Y (%) | | 66.0 | |

*SM = Starting material - [6,7-Dimethoxy-3,4-dihydro isoquinoline];
EA = Ethyl Acetate;
The diastereomer impurity is the (RS, SR) diastereomer of $d_6$-tetrabenazine.

TABLE 27

Optimization of the reaction by varying the reaction time

| Exp. No. | Batch Size | Reaction Conditions | Product Quantity | Product Yield | HPLC Purity |
|---|---|---|---|---|---|
| 1 | 10 g | 6,7-Dimethoxy-3,4-dihydroisoquinoline hydrochloride (1 eq) 2-acetyl-N,N,N,4-tetramethyl-1-pentanaminium iodide (1.08 eq) Methanol/water (3:1) (6 vol) $K_2CO_3$ (1 eq) 45-50° C., 24 hour | 8.5 g | 61% | 99.2% |
| 2 | 10 g | 6,7-Dimethoxy-3,4-dihydroisoquinoline hydrochloride (1 eq) 2-acetyl-N,N,N,4-tetramethyl-1-pentanaminium iodide (1.08 eq) Methanol/water (3:1) (6 vol) $K_2CO_3$ (1 eq) 45-50° C., 48 hour | 9.4 g | 67.4% | 99.5% |
| 3 | 10 g | 6,7-Dimethoxy-3,4-dihydroisoquinoline hydrochloride (1 eq) 2-acetyl-N,N,N,4-tetramethyl-1-pentanaminium iodide (1.08 eq) Methanol/water (3:1) (6 vol) $K_2CO_3$ (1 eq) 45-50° C., 63 hour | 9.2 g | 66% | 99.2% |

TABLE 30

Comparison of $d_0$-6,7-dimethoxy-3,4-dihydroiso-quinoline hydrochloride and $d_6$-6,7-dimethoxy-3,4-dihydroiso-quinoline hydrochloride

| Exp. No. | Batch Size | Reaction Conditions | Product Quantity | Product Yield | HPLC Purity |
|---|---|---|---|---|---|
| 1 | 10 g | $d_0$-6,7-Dimethoxy-3,4-dihydro isoquinoline hydrochloride (1 eq)<br>2-acetyl-N,N,N,4-tetramethyl-1-pentanaminium iodide (1.08 eq)<br>Methanol/water (3:1) (6 vol)<br>$K_2CO_3$ (1 eq)<br>45-50° C., 48 hours | 9.4 g | 67.4% | 99.5% |
| 2 | 10 g | $d_6$-6,7-Dimethoxy-3,4-dihydro isoquinoline hydrochloride (1 eq)<br>2-acetyl-N,N,N,4-tetramethyl-1-pentanaminium iodide (1.08 eq)<br>Methanol/water (3:1) (6 vol)<br>$K_2CO_3$ (1 eq)<br>45-50° C., 48 hours | 9.96 g | 72.0% | 99.9% |
| 3 | 10 g | $d_6$-6,7-Dimethoxy-3,4-dihydro isoquinoline hydrochloride (1 eq)<br>2-acetyl-N,N,N,4-tetramethyl-1-pentanaminium iodide (1.08 eq)<br>Methanol/water (3:1) (6 vol)<br>$K_2CO_3$ (1 eq)<br>45-50° C., 48 hours | 9.4 g | 68.3% | 99.8% |
| 4 | 125 g | $d_6$-6,7-Dimethoxy-3,4-dihydro isoquinoline hydrochloride (1 eq)<br>2-acetyl-N,N,N,4-tetramethyl-1-pentanaminium iodide (1.08 eq)<br>Methanol/water (3:1) (6 vol)<br>$K_2CO_3$ (1 eq)<br>45-50° C., 48 hours | 125.7 g | 72.77% | 99.64% |

TABLE 31

Optimization by varying the purity of 6,7-dimethoxy-3,4-dihydro isoquinoline hydrochloride

| Exp. No. | Batch Size (Purity) | Reaction Conditions | Product Quantity | Product Yield | HPLC Purity |
|---|---|---|---|---|---|
| 1 | 10 g (87.1%) | 6,7-Dimethoxy-3,4-dihydro isoquinoline hydrochloride (1 eq)<br>2-acetyl-N,N,N,4-tetramethyl-1-pentanaminium iodide (1.08 eq)<br>Methanol/water (3:1) (6 vol)<br>$K_2CO_3$ (1 eq)<br>45-50° C., 63 hours | 9.2 g | 66% | 99.5% |
| 2 | 8 g (90.3%) | 6,7-Dimethoxy-3,4-dihydro isoquinoline hydrochloride (1 eq)<br>2-acetyl-N,N,N,4-tetramethyl-1-pentanaminium iodide (1.08 eq)<br>Methanol/water (3:1) (6 vol)<br>$K_2CO_3$ (1 eq)<br>45-50° C., 63 hours | 8.61 g | 77.1% | 99.9% |
| 3 | 4 g (99.0%) | 6,7-Dimethoxy-3,4-dihydro isoquinoline hydrochloride (1 eq)<br>2-acetyl-N,N,N,4-tetramethyl-1-pentanaminium iodide (1.08 eq)<br>Methanol/water (3:1) (6 vol)<br>$K_2CO_3$ (1 eq)<br>45-50° C., 63 hours | 4.72 g | 84.7% | 99.8% |

TABLE 31-continued

Optimization by varying the purity of 6,7-dimethoxy-3,4-dihydro isoquinoline hydrochloride

| Exp. No. | Batch Size (Purity) | Reaction Conditions | Product Quantity | Product Yield | HPLC Purity |
|---|---|---|---|---|---|
| 4 | 50 g (99.0%) | 6,7-Dimethoxy-3,4-dihydro isoquinoline hydrochloride (1 eq) 2-acetyl-N,N,N,4-tetramethyl-1-pentanaminium iodide (1.08 eq) Methanol/water (3:1) (6 vol) $K_2CO_3$ (1 eq) 45-50° C., 63 hours | 59.7 g | 85.6% | 99.64% |

Representative Example—Step 2

(RR,SS)-1,3,4,6,7-11b-Hexahydro-9,10-di(methoxy-$d_3$)-3-(2-methylpropyl)-2H-benzo[a]quinolizin-2-one The 2-acetyl-N,N,N,4-tetramethyl-1-pentanaminium iodide from step 1 (146 g) was charged to a suspension containing $d_6$-6,7-dimethoxy-3, 4-dihydroisoquinoline hydrochloride (90 g, 0.385 mol, 1.00 eq), methanol (405 mL, 4.5 vol) and water (135 mL, 1.5 vol) at 25-30° C. To the reaction mixture $K_2CO_3$ (54 g, 0.385 mol, 1.00 eq) was added at 25-30° C. and stirred at 40-45° C. for 30 hours. The reaction mixture was cooled and water (270 mL, 3.0 vol) was added. The reaction mass was filtered and the solids were washed with water (270 mL, 3.0 vol) and dried in an oven for 12 hours at 50-55° C. to afford the crude title compound as a light brown powder (100 g, yield=80.6%). $^1$H NMR (300 MHz, CDCl$_3$), δ 6.62 (s, 1H), 6.55 (s, 1H), 3.54 (d, 1H, J=11.7), 3.31 (dd, 1H, J=11.4 and 6.3), 3.11 (m, 2H), 2.92 (dd, 1H, J=13.5 and 3.3), 2.73 (m, 2H), 2.59 (m, 2H), 2.39 (t, 1H, J=11.7), 1.82 (m, 1H), 1.65 (m, 1H), 1.03 (m, 1H), 0.90 (m, 6H); LC-MS: m/z=324.18 (MH)$^+$.

Step 3—Purification of (RR,SS)-1,3,4,6,7-11b-Hexahydro-9,10-di(methoxy-$d_3$)-3-(2-methylpropyl)-2H-benzo[a]quinolizin-2-one Representative Example Crude (RR, SS)-1,3,4,6,7-11b-Hexahydro-9,10-di(methoxy-$d_3$)-3-(2-methylpropyl)-2H-benzo[a]quinolizin-2-one from step 2 (90 g) was charged into absolute ethanol (540 mL, 6.0 vol) and heated to 75-85° C. for 1 hour. The reaction mass was filtered through a Buchner funnel at 75-85° C. and the filter cake was washed with hot ethanol (45 mL, 0.5 vol). The filtrate was cooled to 25-30° C. over 4 hours and further cooled to 0-5° C. over 3-4 hours. The resulting solid was filtered, washed with cold ethanol (180 mL, 2.0 vol), and dried under vacuum to afford the title compound as a pale yellow crystalline powder (75 g, yield=83.3%). $^1$H NMR (300 MHz, CDCl$_3$), δ 6.62 (s, 1H), 6.55 (s, 1H), 3.54 (d, 1H, J=11.7), 3.31 (dd, 1H, J=11.4 and 6.3), 3.11 (m, 2H), 2.92 (dd, 1H, J=13.5 and 3.3), 2.73 (m, 2H), 2.59 (m, 2H), 2.39 (t, 1H, J=11.7), 1.82 (m, 1H), 1.65 (m, 1H), 1.03 (m, 1H), 0.90 (m, 6H); LC-MS: m/z=324.18 (MH)$^+$.

EXAMPLE 4

3-[(Dimethylamino)methyl]-5-methyl-hexan-2-one

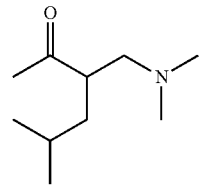

Step 1

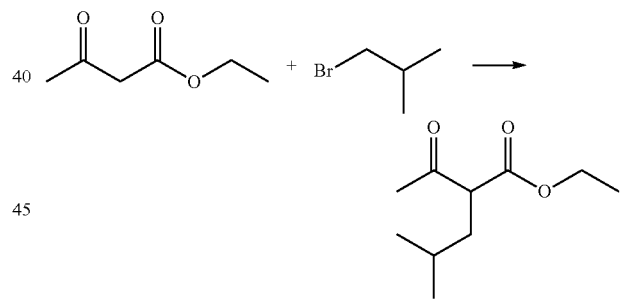

2-Acetyl-4-methylpentanoic acid ethyl ester

To a solution of ethyl acetoacetate (500 g, 3.842 mol, 1.00 eq) in DMF (1.5 L, 3.0 vol), KI (63.7 g, 0.384 mol, 0.10 eq), tetrabutylammonium bromide (136 g, 0.422 mol, 0.11 eq) and $K_2CO_3$ (632 g, 4.572 mol, 1.19 eq) were charged at 25-35° C. The reaction mixture was heated to 40-50° C. and 1-bromo 2-methyl propane (579 g, 4.226 mol, 1.10 eq) was added over 1 hour. The reaction mixture was heated to 65-75° C. for 6 hours, cooled and quenched with water (5.0 L, 10.0 vol). The reaction mixture was extracted with toluene (2×2.0 L, 2×4.0 vol) and the combined organic layers were washed with water (2×1.5 L, 2×3.0 vol). The organic layer was evaporated under reduced pressure to obtain crude 2-acetyl-4-methylpentanoic acid ethyl ester.

Step 2

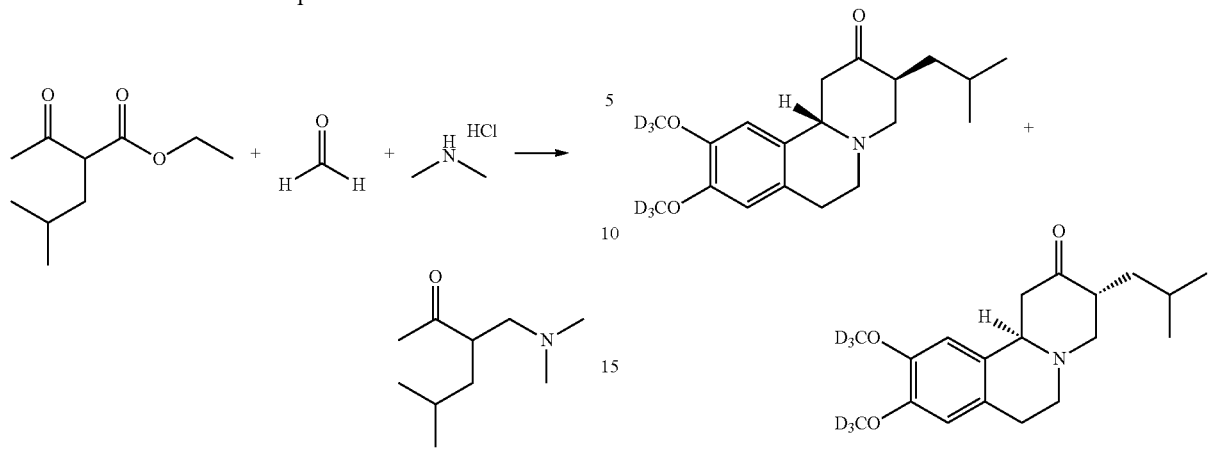

3-[(Dimethylamino)methyl]-5-methyl-hexan-2-one

The ester was hydrolyzed using potassium hydroxide (212 g, 3.78 mol, 1.1 eq) in water (3.84 L, 6.0 vol). After the hydrolysis, the reaction mixture was washed with methyl tert-butyl ether (2×2.56 L, 2×4.0 vol) and the pH of the reaction mixture was adjusted to 6.8-7.2 using concentrated HCl (96 mL, 0.15 vol). Dimethylamine hydrochloride solution (420 g, 5.16 mol, 1.50 eq dissolved in 0.224 L, 0.35 vol of purified water), and formaldehyde solution (0.428 L, 5.763 mol, 1.675 eq) and tetrabutylammonium bromide (110 g, 0.344 mol, 0.10 eq) were added to the reaction mixture, and the pH was adjusted to below 1 using concentrated HCl (0.352 L, 0.55 vol) over 1 hour at 25-35° C. The reaction mixture was stirred for 15 hours at 25-35° C. and the pH was adjusted to 12.0-13.0 using 20% aqueous KOH (3.20 L, 5.0 vol) solution at 25-35° C. and dimethylamine hydrochloride (420 g, 5.16 mol, 1.5 eq) was added. The reaction mixture was stirred for 36 hours at 25-35° C. and the pH of the reaction mixture was adjust to below 1 using concentrated HCl (0.84 L, 0.13 vol) at 25-35° C. over 1 h. The reaction mixture was washed with methyl tert-butyl ether (2×2.56 L, 2×4.0 vol) and the pH of the reaction mixture was adjusted to 9-10 by using 20% aqueous KOH solution (1.72 L, 2.68 vol) at 25-35° C. The product was extracted with ethyl acetate (2×2.56 L, 2×4.0 vol and 1×1.28 L, 1×2.0 vol) and the combined organic layers were washed sequentially with purified water (2×1.92 L, 2×3.0 vol) and 10% ammonium chloride solution (2×3.2 L, 2×5.0 vol). Activated carbon (32 g, 0.05% w/w) was added to the organic layer and the mixture was stirred for 30-45 minutes at 25-35° C. The organic layer was filtered through celite (106 g) and was washed with ethyl acetate (0.32 L, 0.5 vol). The filtrate was distilled under reduced pressure to afford the title compound as a pale yellow liquid (151 g, yield=22.3%). $^1$H NMR (300 MHz, CDCl$_3$), δ 2.7-2.85 (m, 1H), 2.56-2.6 (m, 1H), 2.16 (s, 7H), 2.13 (s, 3H), 1.12-1.55 (m, 3H), 0.92 (d, 3H), 0.89 (d, 3H); LC-MS: m/z=172.11 (MH)$^+$.

From the foregoing description, one skilled in the art can ascertain the essential characteristics of this invention, and without departing from the spirit and scope thereof, can make various changes and modifications of the invention to adapt it to various usages and conditions.

What is claimed is:
1. A process of preparing a racemic mixture of (RR,SS)-d$_6$-tetrabenazine

(RR, SS)-d$_6$-tetrabenazine
wherein the deuterium enrichment of the (RR, SS)-d$_6$-tetrabenazine is no less than about 10%, comprising:
reacting d$_6$-6,7-dimethoxy-3,4-dihydroisoquinoline, or a salt thereof:

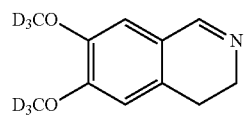

d$_6$-6,7-dimethoxy-3,4-dihydroisoquinoline
with a salt of 2-acetyl-N,N,N,4-tetramethyl-1-pentan-aminium:

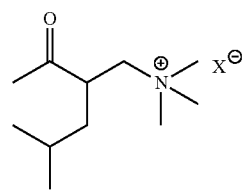

wherein X is halogen, alkyl sulfate, alkyl sulfonate, halosulfonate, perhaloalkyl sulfonate, aryl sulfonate, alkylaryl sulfonate, dialkyloxonium, alkylphosphate, or alkyl carbonate;
and an optional base;
in the presence of a solvent mixture that is a combination of water and an alcohol that is methanol or ethanol;
for a period of time and at a temperature sufficient to produce the (RR,SS)-d$_6$-tetrabenazine having a diastereomeric purity of at least 99%, based on high performance liquid chromatography.

2. The process of claim 1, wherein the solvent mixture is a combination of methanol and water.

3. The process of claim 2, wherein the ratio of methanol:water is about 5:1 to about 1:1.

4. The process of claim 2, wherein the ratio of methanol:water is about 3:1.

5. The process of claim 2, wherein the ratio of methanol:water is about 1:1.

6. The process of claim 1, wherein the solvent mixture is a combination of ethanol and water.

7. The process of claim 1, wherein the $d_6$-6,7-dimethoxy-3,4-dihydroisoquinoline is a salt form of $d_6$-6,7-dimethoxy-3,4-dihydroisoquinoline.

8. The process of claim 7, wherein the salt form of $d_6$-6,7-dimethoxy-3,4-dihydroisoquinoline is $d_6$-6,7-dimethoxy-3,4-dihydroisoquinoline hydrochloride.

9. The process of claim 8, wherein the process is carried out in the presence of a base.

10. The process of claim 9, wherein the base is $K_2CO_3$.

11. The process of claim 1, wherein X is halogen.

12. The process of claim 11, wherein the halogen is iodide.

13. The process of claim 1, wherein the period of time is about 24 hours to about 63 hours.

14. The process of claim 1, wherein the temperature is about 40° C. to about 60° C.

15. The process of claim 1, wherein the diastereomeric purity is at least 99.1%.

16. The process of claim 1, wherein the diastereomeric purity is at least 99.2%.

17. The process of claim 1, wherein the diastereomeric purity is at least 99.5%.

18. The process of claim 1, wherein the diastereomeric purity is at least 99.6%.

19. The process of claim 1, wherein the diastereomeric purity is at least 99.9%.

20. The process of claim 1, wherein the deuterium enrichment of the (RR,SS)-$d_6$-tetrabenazine is no less than about 50%.

21. The process of claim 1, wherein the deuterium enrichment of the (RR,SS)-$d_6$-tetrabenazine is no less than about 90%.

22. The process of claim 1, wherein the deuterium enrichment of the (RR,SS)-$d_6$-tetrabenazine is no less than about 98%.

23. The process of claim 4, wherein a salt form of $d_6$-6,7-dimethoxy-3,4-dihydroisoquinoline is reacted and the salt form is $d_6$-6,7-dimethoxy-3,4-dihydroisoquinoline hydrochloride.

24. The process of claim 23, wherein the process is carried out in the presence of $K_2CO_3$.

25. The process of claim 24, wherein X is halogen.

26. The process of claim 25, wherein the halogen is iodide.

27. The process of claim 26, wherein the diastereomeric purity is at least 99.1%.

28. The process of claim 4, wherein X is halogen.

29. The process of claim 28, wherein the halogen is iodide.

30. The process of claim 4, wherein the deuterium enrichment of the (RR,SS)-$d_6$-tetrabenazine is no less than about 50%.

31. The process of claim 4, wherein the deuterium enrichment of the (RR,SS)-$d_6$-tetrabenazine is no less than about 90%.

32. The process of claim 4, wherein the deuterium enrichment of the (RR,SS)-$d_6$-tetrabenazine is no less than about 98%.

33. The process of claim 23, wherein the deuterium enrichment of the (RR,SS)-$d_6$-tetrabenazine is no less than about 50%.

34. The process of claim 23, wherein the deuterium enrichment of the (RR,SS)-$d_6$-tetrabenazine is no less than about 90%.

35. The process of claim 23, wherein the deuterium enrichment of the (RR,SS)-$d_6$-tetrabenazine is no less than about 98%.

36. The process of claim 4, wherein a salt form of $d_6$-6,7-dimethoxy-3,4-dihydroisoquinoline is reacted and the salt form is $d_6$-6,7-dimethoxy-3,4-dihydroisoquinoline hydrochloride, X is iodide, and the diastereomeric purity is at least 99.1.

37. The process of claim 36, wherein the process is carried out in the presence of $K_2CO_3$.

* * * * *